United States Patent
Moormann et al.

[11] Patent Number: 6,159,011
[45] Date of Patent: Dec. 12, 2000

[54] PROCESS FOR PRODUCING A TITANIUM-CERAMIC ADHESIVE COMPOSITE SYSTEM

[76] Inventors: Andreas Moormann, Lübecker Strasse 51, D-10559 Berlin; Lothar Wehnert, Angerburger Allee 35, D-14055 Berlin, both of Germany

[21] Appl. No.: 09/202,744

[22] PCT Filed: Jun. 19, 1997

[86] PCT No.: PCT/DE97/01343

§ 371 Date: Jan. 27, 1999

§ 102(e) Date: Jan. 27, 1999

[87] PCT Pub. No.: WO97/48835

PCT Pub. Date: Dec. 24, 1997

[30] Foreign Application Priority Data

Jun. 20, 1996 [DE] Germany ............... 196 26 440

[51] Int. Cl.$^7$ .................. C23C 14/48; A61K 6/06
[52] U.S. Cl. .................. 433/226; 433/206; 156/272.2
[58] Field of Search ................ 433/180, 206, 433/226, 228.1; 156/272.2

[56] References Cited

U.S. PATENT DOCUMENTS 5,534,103  7/1996  Yano et al. ............ 156/272.2

FOREIGN PATENT DOCUMENTS

| 90 05 995 | 10/1990 | Germany. |
| 62-174377 | 7/1987 | Japan. |
| 2-85374 | 3/1990 | Japan. |
| 4-107259 | 4/1992 | Japan. |

*Primary Examiner*—Ralph A. Lewis
*Attorney, Agent, or Firm*—Herbert Dubno

[57] ABSTRACT

The invention relates to a process for producing a titanium and ceramic adhesive composite system, and a titanium and ceramic adhesive system produced therefrom. The system can be used to improve the adhesive of ceramics, intended for pure titanium or titanium alloys, to a structure consisting of pure titanium or a titanium alloy. The improvement is attained in that silicon ions (4) are inserted into the surface (1) of a structure consisting of pure titanium or a titanium alloy by ion implantation with ion beams (3) between the atoms (5) of the titanium or the atoms (5) of the titanium alloy. The silicon ions form a titanium and silicon layer (2) in the surface (1) of the structure in the penetration layer of the ion implantation, on which titanium and silicon layer crystalline, non-metallic inorganic materials are applied, and an adhesive composite is produced with said materials.

39 Claims, 11 Drawing Sheets

PROCESS FOR PRODUCING A TITANIUM-CERAMIC ADHESIVE COMPOSITE SYSTEM

The invention relates to the production of a titanium-ceramic adhesive composite system and to a titanium-ceramic adhesive composite system produced thereby.

It is known to use titanium or titanium alloys as a material for industrial objects which need to have high strength and low weight. It is therefore used in the car industry and in air and space travel, e.g. for engines and power units. Titanium, particularly at elevated temperature in air, becomes coated with a firmly-adhering, hard, brittle oxide layer. The oxide layer due to oxygen diffusion makes it difficult to apply other substances to the titanium surface, particularly when producing a titanium-ceramic adhesive composite system. Owing to the low coefficient of thermal expansion of titanium, veneering titanium structures with ceramic materials results not only in crazing but also in large-area flaking of the ceramic layer.

The problem will now be discussed in greater detail with reference to the development in the area of the use of titanium-ceramic adhesive composite systems in dental technology.

It is known to replace expensive noble metal-containing alloys for dental prostheses by gold-reduced alloys, palladium-based alloys or alloys free from noble metals.

Owing to the increasing awareness of patients of the allergenic effects of dental materials and to the frequent allergic reactions of patients after incorporation of dental prostheses, the need to find a suitable material has been recognised. Non-alloyed titanium is a suitable material in this regard. It has given good results as a material in general medical use and also, in recent decades, in dental implants and surgery. Its most important properties include high biocompatability, low cost, and high availability owing to its frequency of occurrence.

Various material properties of titanium resulted in initial difficulties in processing for dental purposes, but these were overcome by suitable measures. Dental casting of titanium has become possible through development of special casting systems and suitable embedding materials. The ability to be veneered with ceramics, an important precondition for general use of a dental material, was achieved only after development of low-melting ceramic materials having a suitable thermal expansion coefficient. Subsequent clinical tests confirm in-vitro tests, in which the loss of adhesive strength was determined after cyclic changes in temperature load. The difficulty is increased by the fact that the initial adhesive strength of titanium-ceramic combinations in the various mechanical breaking tests was found to be lower than for conventional metal-ceramic systems.

The proportions of faulty ceramic titanium veneers found in the clinical tests was assumed to be due to the losses in adhesive strength measured in vitro as a result of changes in temperature load (MOORMANN, A.: Vergleichende Untersuchengen zue Verbundfestigkeit von neun Titan-Keramik-Verbundkombi-nationen in Abhangigkeit von den Lagerungsbedingungen, Med Diss, Berlin 1993).

After a usable process of titanium casting was developed, there was an increase in the range of applications of titanium in dentistry. It is used in prostheses and implants and also in endodontics as a dowel material and for trans-dental fixing. In orthopedic jaw therapy with fixed appliances and in conservative dentistry, titanium alloys are also used as a material for inlays, on-lays and, increasingly frequently, for part-crowns.

To meet aesthetic requirements, it is important for a dental prosthetic material to be capable of having a tooth-colour veneer. A reliable ceramic veneerability is an essential condition for universal use of a prosthetic material.

The main components of dental ceramic materials are:
about 80% glassy feldspar ($6SiO_2$—$Al_2O_3$—$K_2$))
about 15 to 20% quartz ($SiO_2$) and
about 0 to 10% clay minerals, e.g. kaolin.

Glassy feldspar serves as a flux and influences the transparency of the ceramic. Kaolin, like quartz, increases the strength of the ceramics, and quartz also increases the transparency.

During the firing process, the dental ceramic melts, when the added $SiO_2$ and $B_2O_3$ oxides form a glassy matrix in which leucite crystals are incorporated. Incompletely melted components are in the form of a sinter phase. Accordingly, fired dental metal ceramic consists of a glass, a sinter and a crystal phase.

Owing to the need to match thermal expansion coefficients of the metal and the ceramic, it is necessary to modify the crystal phase. Since metals have a very high thermal expansion coefficient compared with glass, the proportion of glass to ceramic, (leucite) in the ceramic material must be matched to that of the respective alloy.

In connection with the use of pure titanium for production of dental prostheses, novel ceramic materials have been developed, especially adapted to the requirements of titanium.

Owing to the low thermal coefficients compared with conventional dental firing alloys, the high affinity for oxygen and the allotropic conversion of the lattice structure at 882.5° C., it was necessary to develop ceramics having different properties from normal ceramics. Owing to the low thermal expansion coefficients of titanium, veneering of titanium skeletons with conventional ceramic materials results not only in crazing but also in large-area flaking of the ceramic layer (LINDIGKEIT, J.: Werkstoffkunde und Technologie, In: SITBERT, G. K.: Dentallegierungen in der zahnärztichen Praxis, Hanser, Munich—Vienna 1989).

The thermal expansion coefficient was adapted, reducing the value by 30%, by increasing the glass content, replacing leucite by mullite, an aluminum silicate.

The sinter temperature was reduced by 150 to 200° C. by increasing the content of sodium oxide ($Na_2O$) and reducing the content of aluminum oxide ($Al_2O_3$).

The high affinity for oxygen or tendency to oxidation necessitates use of special bonders which are designed to dissolve or enclose oxides already present on the titanium surface and, owing to their glassy nature, provide a seal against further oxidation.

The changes described in the composition of the titanium-ceramic veneering materials do not affect either their resistance to hydrolysis or their bonding strength.

There is relatively little knowledge of the exact mechanisms of adhesion between conventional stoving of alloys and ceramic materials, and correspondingly there are no complete theories about the bonding between titanium and the corresponding ceramic veneering materials. There are contradictory views on the subject in the relevant literature.

In addition to the general assumption that the mechanisms described in the previous section are also involved in the bonding of titanium to ceramics, research is also directed towards various aspects, in some cases very specific, of the corresponding mechanisms.

MOOMANN, in his Med. Diss., Berlin 1993 starts from the assumption that the titanium-ceramic adhesive bond is due initially to the formation of an oxidic flaky crystalline intermediate layer (probably mainly consisting of $TiSi_3$ and of oxides, particularly in the region of the surface titanium layer) in the contact zone between titanium and ceramic. Owing to the high reactivity of titanium even after the ceramic firing process, the said zone also undergoes chemical charges in the sense of progressive oxygen embrittlement of the surface titanium layer, which MOORMANN thinks is the cause of the failure of the bond.

In addition to development of suitable titanium ceramics having lower sinter temperatures and lower thermal coefficients of expansion adapted to requirements, as described, special bonders have been developed which, owing to their reduced properties, dissolve existing oxide layers on the titanium surface or enclose the oxides and act as a seal which is designed to prevent a new oxide layer from forming in the metal-ceramic interface during the firing process.

Titanium has been veneered with ceramics in a protective gas atmosphere, likewise with the object of avoiding the formation of titanium oxides during ceramic firing.

To prevent the α-case from weakening the bond, it is recommended to use embedding materials especially developed for dental casting, to avoid a thick layer of α-case, and to remove this layer completely from the surface for veneering.

In order completely to avoid an α-case and to obtain a workpiece free from cavities, dental workpieces can be produced from prefabricated titanium semifinished structures by CAD-CAM techniques or spark erosion or a combination of both techniques.

The extent to which elements stabilizing the α-phase of titanium also influence the adhesive bond between titanium and ceramic was investigated by MOORMANN using a titanium-aluminum alloy (MOORMANN, A.: Vergleichende Untersuchengen zur Verbundfestigkeit von neun Titan-Keramik-Verbundkombi-nationen in Abhëngigkeit von den Lagerungsbedingungen Med Diss, Berlin 1993).

POTTHOFF investigated the PROBOND process as applied to titanium bridge skeletons (POTTHOFF, D.: Beigefestigkeits-und Randspaltuntersuchung von metallkeramischen Seiten-zahnbrëken-Probondverfahren and konventionells Verfahren, Zahnmed Diss, FU-Berlin 1994).

The possibility of improving the titanium-ceramic adhesive bond by mechanical surface machining by precision grinding with various grain sizes (F 80 and F 220) and subsequent blasting with conundrum (grain size 250 µm) was investigated by TESCH et al. (TESCH. H.: PASSLER. V.; MANN, E.; Untersuchengen zum Titan-Keramik Verbund dentallabor XLI, 1/93, 71–74).

ECKMANN investigated the influence of mechanical retention (retention beads) or of surface titanium plasma coating on the adhesive bond between titanium and ceramic (ECKMANN, St,: Untersuchungen zur Beigefestigkeit des Titan-Keramik-Verbundes bei Brücken in Abhangidkeit von der Ober-flächenbearbeitung sowie zur Paßgenauigkeit Zahnmed Diss, Berlin 1994).

DERAND and HERO tried to improve the adhesive bond by use of a special gold bonder. DERAND, T.; HERO.: Bond strength of porcelain on cast versus wrought titanium Scand J Dent Res 100, 1844–188 (1992).

KRUSE and BAUMANN investigated the influence of varying firing temperatures on the adhesive strength of ceramic on titanium (KRUSE, N.: Untersuchung zur Abscherfestigkeit des Titan-Keramik-Verbundes bei fënf Titankeramischen Systeman in Abhängigketi verschiedener Aufbrenntemperatren—Eine in—Vitro-Studie—, Zahnmed Diax, Berlin, 1995; BAUMANN, W.: Bruchmechanische Haftfestigkeitsbestimmung von Verblend-metall-Keramik suf Titan, Med Diss, Aachan 1992).

In spite of this large number of attempts to improve the titanium-ceramic adhesive bond, no success has been obtained in giving equivalent reliability to dental stoving alloys, as confirmed by various clinical longitudinal studies.

The object of the invention is to devise a process for producing a titanium-ceramic adhesive composite system and a titanium-composite adhesive composite system resulting therefrom and adapted to improve the adhesive strength of pure titanium or titanium alloys in the case of certain ceramics on a pure titanium or titanium-alloy structure.

According to the invention, the improvement is obtained by the fact that silicon ions are introduced into the surface of a pure titanium or titanium-alloy structure by ion implantation with ion beams between the atoms of the titanium or the atoms of the titanium alloy, by means of which a titanium-silicon layer is formed in the surface of the structure in the penetration layer of ion implantation, and crystalline non-metallic inorganic materials are thermally applied on to the titanium-silicon layer and an adhesive bond is made with the materials.

Preferably, the silicone ions are incorporated in the form of silicon aggregates in the titanium-silicon layer.

Advantageously, the crystalline non-metallic inorganic materials consist of glass-ceramic materials, non-oxidic ceramic materials or oxidic ceramic materials.

Optionally, the titanium alloy used is a titanium-vanadium-aluminum alloy having the following composition:

Ti—6Al—4V

If required, the titanium alloy is a titanium alloy conforming to the special requirements of the application and the possible production technique.

Advantageously, the implantation of silicon ions into the surface of pure titanium or titanium-alloy structure is performed at an ion dosage of $1\times10^8$ to $1\times10^{18}$ atoms/cm$^2$ and an ion energy of 30 to 400 KeV.

Preferably, the implantation of silicon ions into the surface of the pure titanium or titanium-alloy structure is performed at an ion dosage of $9\times10^{16}$ atoms/cm$^2$ and an ion energy of 150 KeV.

By means of the solution according to the invention, an increase is obtained in the adhesive strength of the crystalline, non-metallic inorganic material used for pure titanium or a titanium alloy.

In particular, a reduction is made in the temperature load cycle resulting from prolonged use of workpieces made therefrom.

In a preferred embodiment of the invention, for use in a dental prosthesis, silicon ions are introduced into the surface of a pure titanium structure by ion implantation with ion beams between the atoms of titanium, as a result of which a titanium-silicon layer is formed in the surface of the structure in the penetration layer of the ion implantation, and a dental ceramic for titanium veneering is fired on the titanium-silicon layer.

An ion dosage of $1\times10^{12}$ to $1\times10^{18}$ atoms/cm$^2$ and an ion energy of 30 to 400 KeV is particularly suitable for implantation of silicon ions into the surface of the pure titanium structure.

Preferably, the implantation of silicon ions into the surface of the pure titanium structure is carried out at an ion dosage of $3\times10^{17}$ atoms/cm$^2$ and an ion energy of 150 KeV.

In accordance with the experiments carried out, the pure titanium can contain the following proportions (defined by % of mass):

| | |
|---|---|
| $O_{max}$ | 0.12 |
| $N_{max}$ | 0.05 |
| $C_{max}$ | 0.05 |
| $H_{max}$ | 0.013 |
| Ti | Remainder |

It has been found particularly advantageous if before the ion implantation of the surface of the pure titanium structure, the surface titanium oxide layer is removed by machining and is subsequently roughened in a protective gas atmosphere by ground monocrystalline silicon ($Si_{mon}$) having a mesh size of 50 to 300 µm.

Alternatively, after removal of the titanium oxide layer from the surface of the pure titanium structure, the surface is roughened by blasting with corumdum ($\alpha\text{-}Al_2O_3$) having a particle size of 50–250 µm.

By means of the solution according to the invention, the pure titanium structure, before the ion implantation, is completely formed as a base member for a dental prosthesis and, apart from firing on the dental ceramic, no further treatment of the structure is carried out after the titanium-silicon layer has formed in the surface of the structure.

In a preferred embodiment, the titanium-silicon layer is formed in the entire surface of the pure titanium structure formed as the base member for a dental prosthesis, and the dental ceramic for the titanium veneering is fired on individual portions of the surface, the dental ceramic being fired on at least those portions of the base member for a dental prostheses which form the tooth regions and the regions of contact with the mucous membrane.

This keeps down the expense of producing a titanium-ceramic adhesive composite for dental prostheses. This also blocks the escape of titanium ions from the pure titanium structure into the mouth area.

Advantageously, the dental ceramic for the titanium veneering is fired on the titanium-silicon layer in four firing cycles:

1st cycle: bonder and/or wash-firing material;
2nd cycle: base material firing;
3rd cycle: dentine firing;
4th cycle: gloss firing.

In this manner, the dental ceramic can be built up on the titanium silicon layer formed in the surface in conventional manner, following the manufacturer's instructions. There is no need to change the method of firing.

In another preferred embodiment of the invention, for use in a high temperature range from 600 to 3600° C., silicon ions are introduced into the surface of a pure titanium or titanium-alloy structure by ion implantation with ion beams between the atoms of the titanium or the atoms of the titanium alloy, as a result of which a titanium-silicon layer is formed in the surface of the structure in the penetration layer of the ion implantation, and crystalline non-metallic inorganic materials are thermally applied to the titanium-silicon layer and an adhesive bond is made with the materials.

Advantageously, the silicon ions are incorporated in the form of siliocn aggregates in the titanium-silicon layer.

Optionally, the crystalline non-metallic inorganic materials consist of glass-ceramic materials, non-oxidic ceramic materials of oxidic ceramic materials.

Advantageously, the implantation of silicon ions into the surface of the pure titanium or titanium-alloy structure is performed at an ion dosage of $1 \times 10^8$ to $1 \times 10^{18}$ atoms/cm² and an ion energy of 30 to 400 KeV.

Optionally, the implantation of silicon ions into the surface of the pure titanium or titanium alloy structure is performed at an ion dosage of $9 \times 10^{16}$ atoms/cm² and an ion energy of 150 KeV.

Preferably, before the ion implantation, the pure titanium or titanium-alloy structure is made in the form of a workpiece for use in a high-temperature range of 600 to 1600° C. and, apart from thermal application of a crystalline non-metallic inorganic material, no further treatment of the structure is carried out after the titanium-silicon layer has been formed in the surface of the structure.

Optionally, the workpiece is used in engines and power units of motor vehicles and in air and space travel.

According to another feature, the invention covers a titanium-ceramic adhesive composite system wherein the surface of a pure titanium or titanium-alloy structure is made in the form of a titanium-silicon layer, the silicon ions being introduced by ion implantation between the atoms of the titanium or the atoms of the titanium alloy and wherein a crystalline non-metallic inorganic material is thermally deposited on to the titanium-silicon layer.

Preferably, the silicon ions for producing the titanium-silicon layer are introduced into the surface of the pure titanium or titanium-alloy structure at an ion dosage of $1 \times 10^8$ to $1 \times 10^{18}$ atoms/cm² and an ion energy of 30 to 400 KeV.

Preferably, the silicon ions are introduced into the surface of the pure titanium or titanium-alloy structure at an ion dosage of $9 \times 10^{16}$ atoms/cm² and an ion energy of 150 KeV.

The titanium-ceramic adhesive composite system according to the invention can be designed for use for a dental prosthesis wherein the surface of a pure titanium structure is in the form of a titanium-silicon layer, silicon ions being introduced by ion implantation between the pure titanium atoms and wherein a dental ceramic for titanium veneering is fired on the titanium-silicon layer.

Preferably, the silicon ions for forming the titanium-silicon layer are introduced into the surface of the pure titanium structure at an ion dosage of $1 \times 10^{12}$ to $1 \times 10^{18}$ atoms/cm² of silicon ions and an ion energy of 30 to 400 KeV.

Optionally, the silicon ions for forming the titanium-silicon layer are introduced into the surface of the pure titanium structure at an ion dosage of $3 \times 10^{17}$ atoms/cm² and an ion energy of 150 KeV.

If required, the pure titanium has the following composition (as % by mass):

| | |
|---|---|
| $O_{max}$ | 0.12 |
| $N_{max}$ | 0.05 |
| $C_{max}$ | 0.06 |
| $H_{max}$ | 0.013 |
| Ti | Remainder |

Advantageously, the pure titanium structure, before its surface has been converted into a titanium-silicon layer, is made completely in the form of a base member for a dental prosthesis, and after the titanium-silicon layer has formed, the dental ceramic is applied thereto by firing in a single treatment operation.

In a preferred embodiment of the titanium-ceramic adhesive composite system, the titanium-silicon layer is formed in the entire surface of the pure titanium structure, which is in the form of the base member for a dental prosthesis, and the dental ceramic intended for the titanium veneering is fired on individual portions of the surface, the dental ceramic being fired at least on those portions of the base member for a dental prosthesis which form the tooth regions and the regions of contact with the mucous membrane.

According to another feature of the invention, the titanium ceramic adhesive composite system is so constructed that for use in a high-temperature range from 600 to 3600° C., the surface of a pure titanium or titanium-alloy structure is formed as a titanium-silicon layer, the silicon ions being introduced by ion implantation between the atoms of the titanium or the atoms of the titanium alloy and wherein a crystalline non-metallic inorganic material is thermally deposited on to the titanium-silicone layer.

Optionally, the silicon ions are incorporated in the form of silicon aggregates into the titanium-silicon layer.

Advantageously, the crystalline non-metallic inorganic materials consist of glass-ceramic materials, non-oxidic ceramic materials or oxidic ceramic materials.

Optionally, the implantation of silicon ions into the surface of the pure titanium or titanium-alloy structure is carried out and an ion dosage of $1 \times 10^8$ to $1 \times 10^{18}$ atoms/cm$^2$ and an ion energy of 30 to 400 KeV.

Advantageously, the implantation of silicon ions into the surface of the pure titanium or titanium-alloy structure is carried out at an ion dosage of $9 \times 10^{16}$ atoms/cm$^2$ and an ion energy of 150 KeV.

Preferably the structure consists of pure titanium or a titanium alloy, and before the ion implantation the structure is constructed as a workpiece for use in a high-temperature range from 600 to 3600° C. and, apart from the thermal application of a crystalline non-metallic inorganic material, no further treatment of the structure is carried out after the titanium-silicon layer forms on the surface of the structure.

The workpiece is usable in engines and power units is motor-vehicle construction and in air and space travel.

The invention will be explained with reference to an exemplified embodiment, In the accompanying drawings:

FIG. 1 diagrammatically shows the surface modification through ion implantation;

Figure 8:
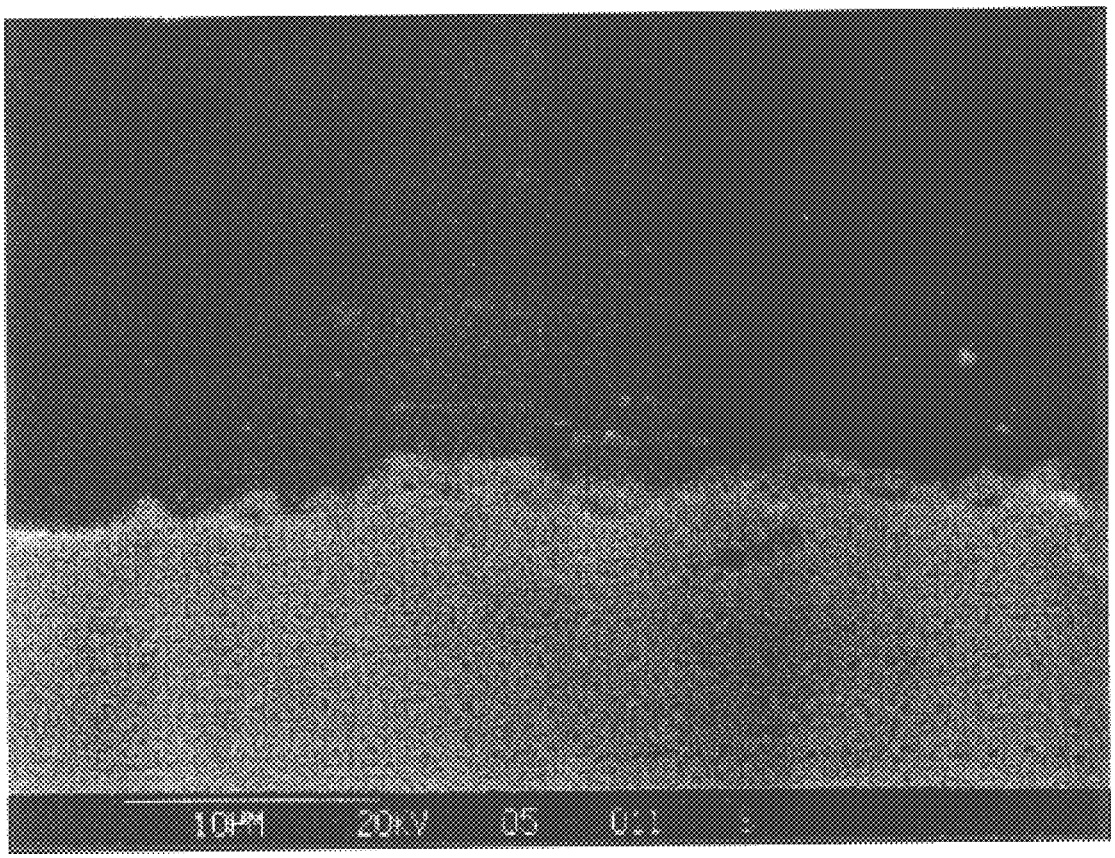
Figure 9:
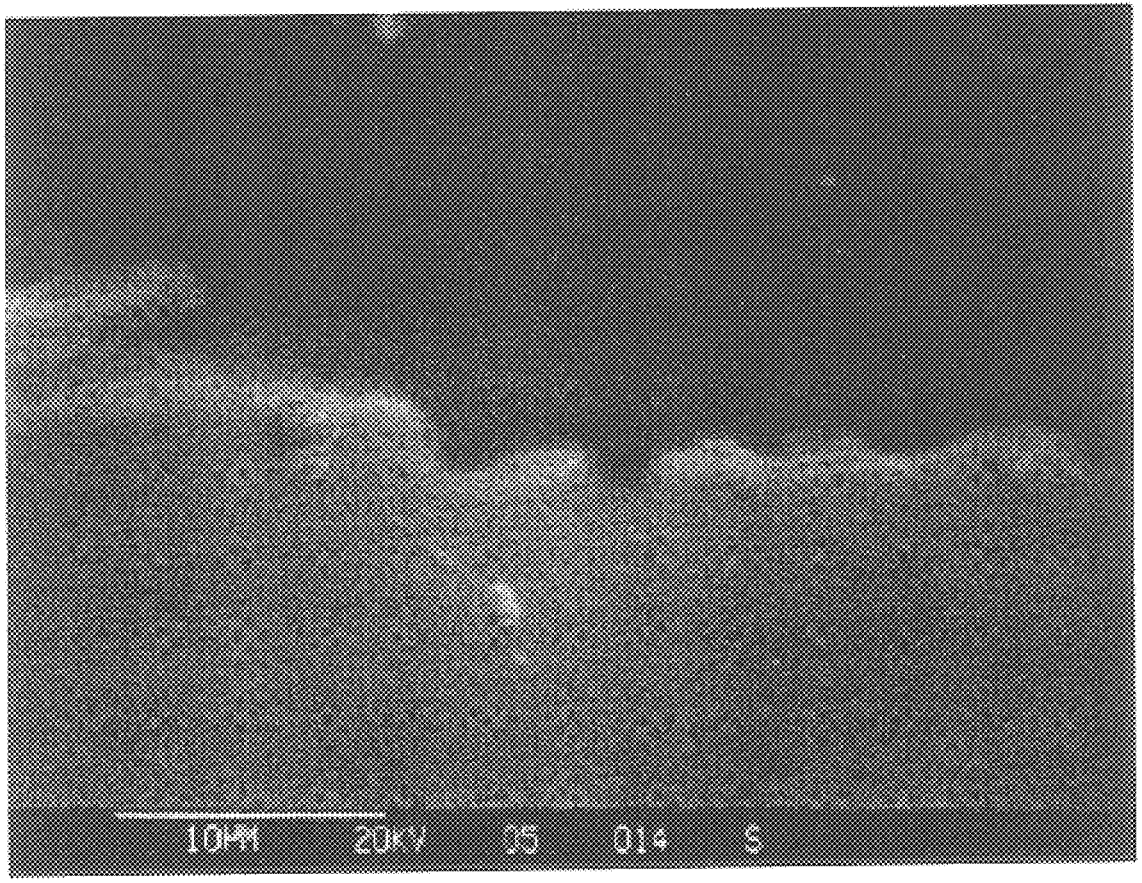
Figure 10:
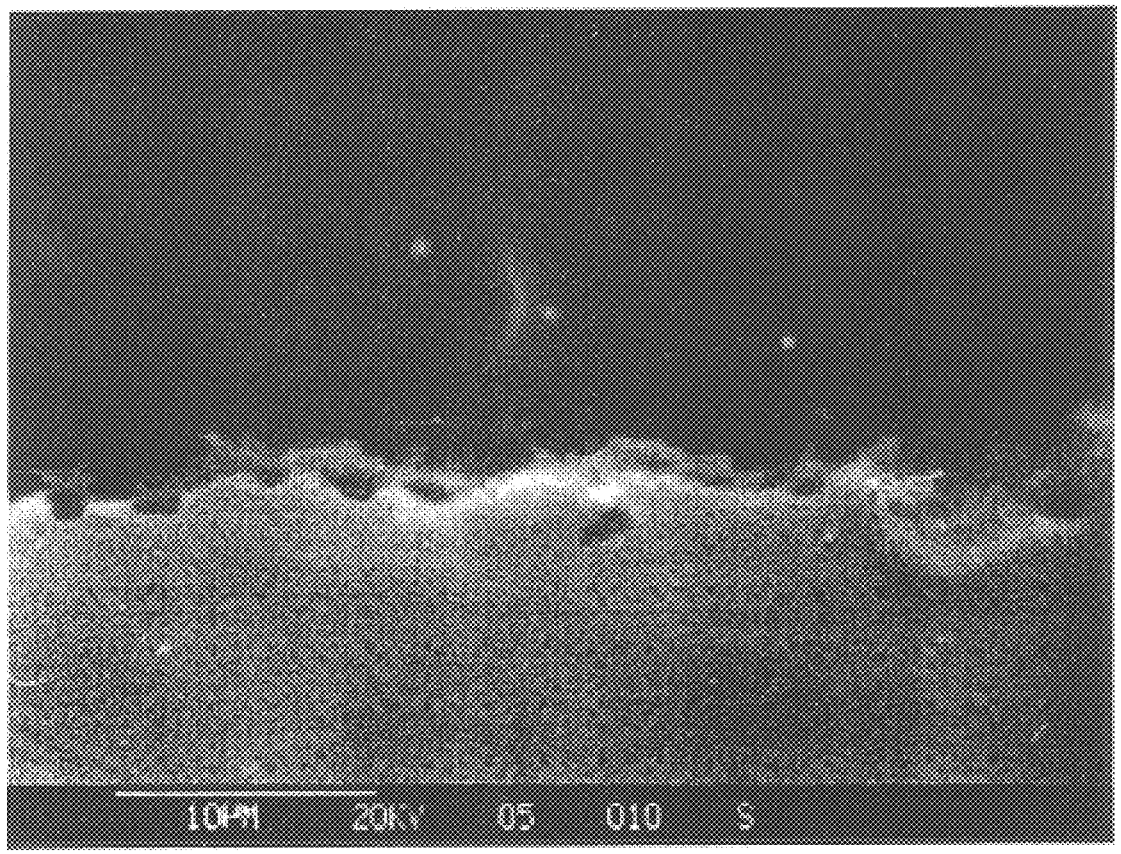
Figure 11:
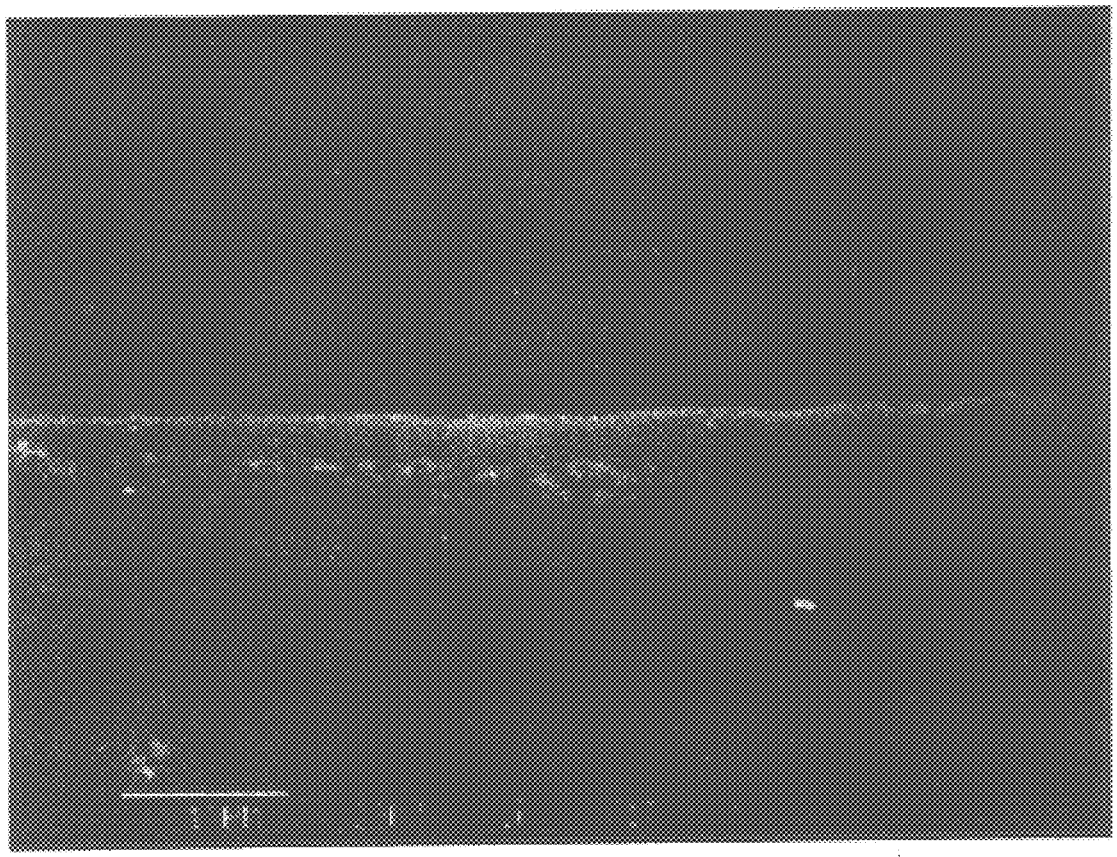
Figure 12:
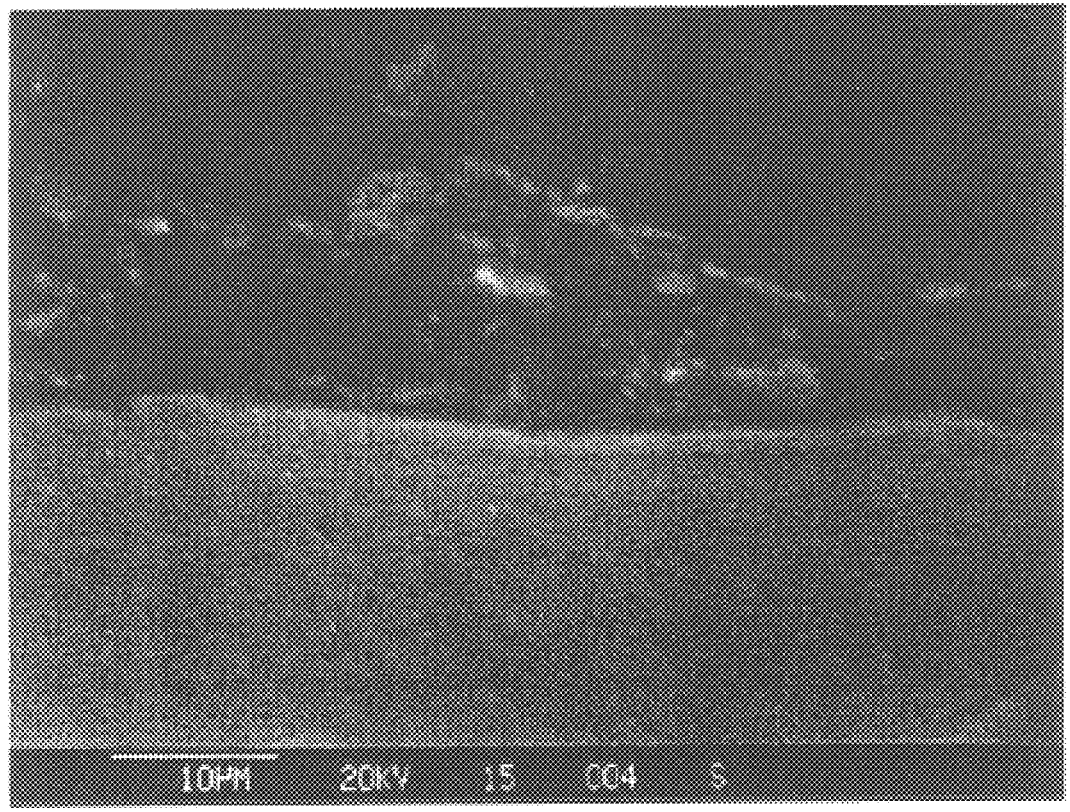

FIG. 8: SEM photograph of the combination: titanium, $\alpha$-AL$_2$O$_3$ treated/TIBOND, TC, magnification 3200:1 without ion implantation;

FIG. 9: REM photograph of the combination: titanium, $\alpha$-al$_2$o$_3$ treated/VITA TITANKERAMIK, TC, magnification 3200:1 with ion implantation;

FIG. 10: REM photograph of the combination: titanium, $\alpha$-Al$_2$O$_3$ treated/VITA TITANKERAMIK, TC, magnification 3200:1 without ion implantation;

FIG. 11: SEM photograph of the combination: titanium, no $\alpha$-Al$_2$O$_3$ treated/TIBOND, TC, magnification: 2000:1 with ion implantation;

FIG. 12: SEM photograph of the combination: titanium, no $\alpha$-Al$_2$O$_3$-treated/TIBOLD, TC, magnification 2000:1 without ion implantation.

Figure 13:
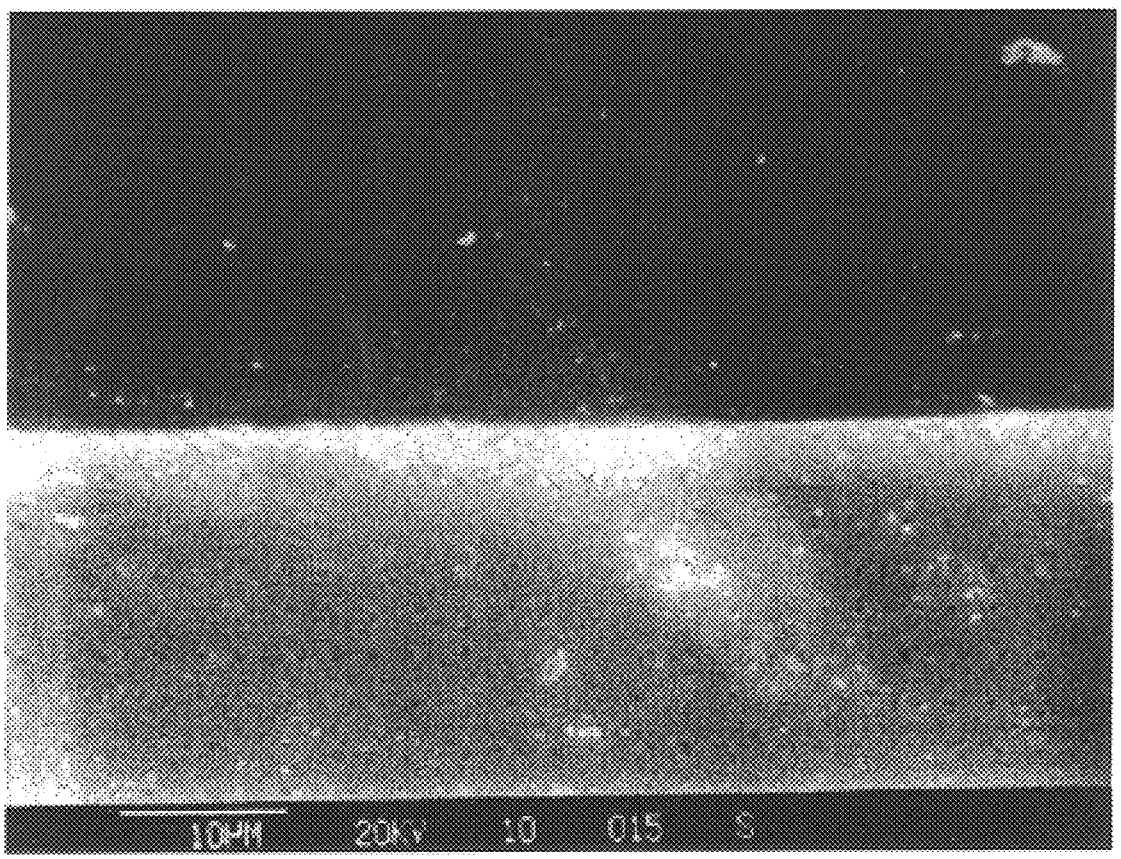
Figure 14:
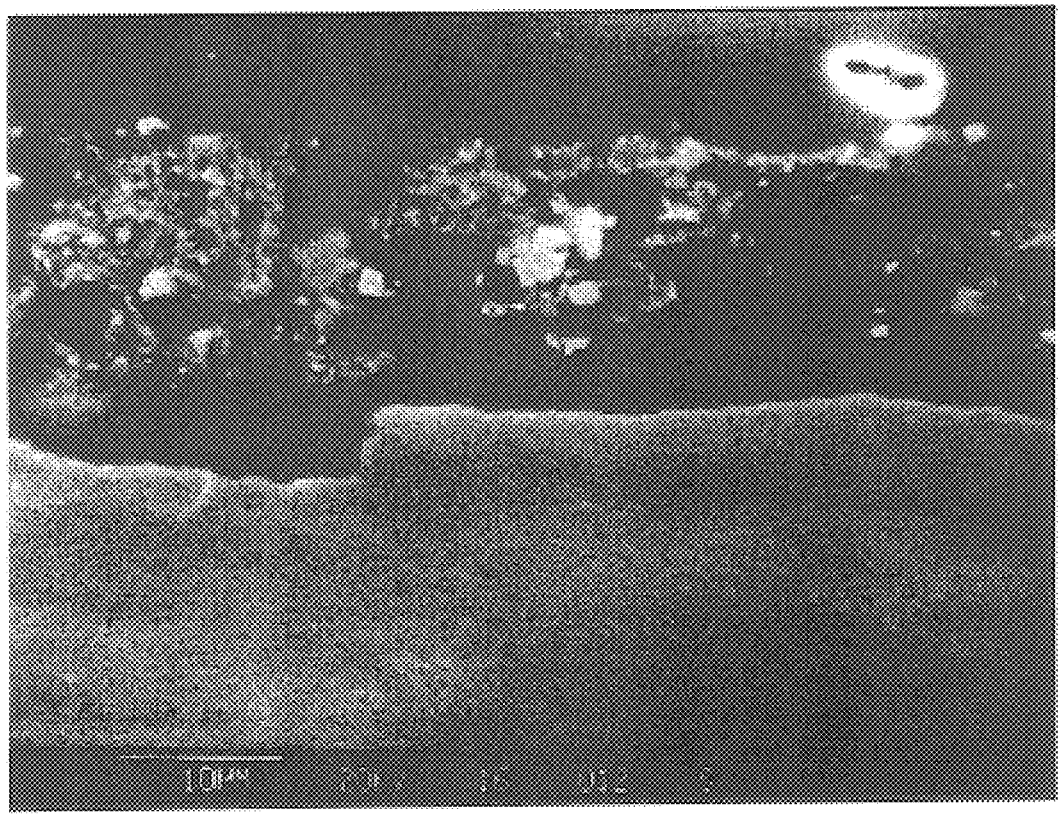

FIG. 13: SEM photograph of the combination: titanium, not $\alpha$-Al$_2$O$_3$ treated/VITA TITANKERAMIK, TC, magnification: 2000:1 with ion implantation;

FIG. 14: SEM photograph of the combination: titanium, not $\alpha$-Al$_2$O$_3$-treated/VITA TITANKERAMIK, TC, magnification 2000:2 without ion implantation.

Figure 1:
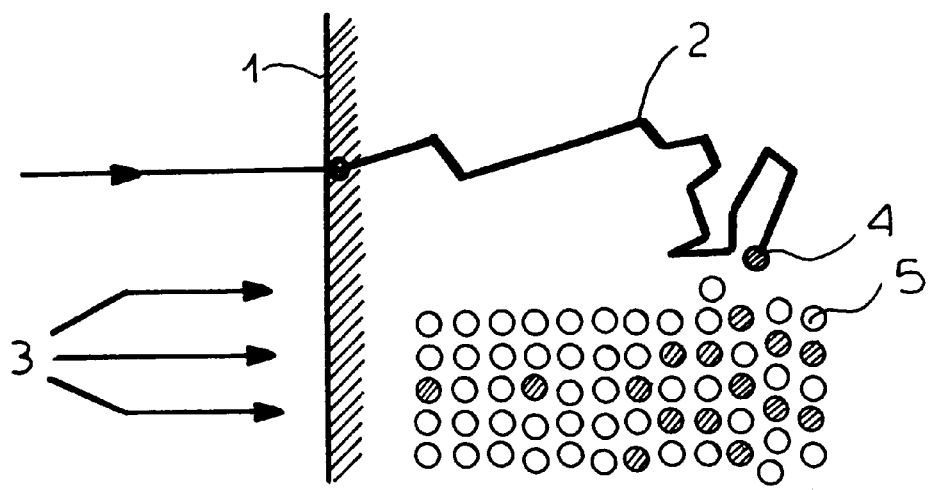

FIG. 1 illustrates processing of titanium by ion implantation. During ion implantation a high-energy ion strikes a sold and results in various interactions with the atoms near the surface. "Titanium∞ hereinafter means either pure titanium or a titanium alloy.

As a result of impacts between the incident ions and the electrons and atomic nuclei in the bombarded material, the ions are deflected from their orbit and described a polygonal orbit and come to rest in a statistical distribution owing to loss of their kinetic energy.

In the process for producing a titanium-ceramic adhesive composite system, during ion implantation silicon ions 4 are introduced in a penetration zone between the titanium atoms 5 by an ion base 3 on to a surface 1 of a titanium structure. In FIG. 1, the silicon ions 4 are shown black and the titanium atoms 5 are white. The result is a titanium-silicon layer 2. The formation of the titanium-silicone layer 2, however, depends on the mass of the silicon ions 4 and titanium atoms 5 and on the implantation parameters, i.e. The ion energies and the ion dosage.

Implantation of siliocn ions 4 in the surface 1 of the titanium structure is effected at an ion dosage of $1 \times 10^8$ to $1 \times 10^{18}$ atom/cm$^2$ and an ion energy of 30 to 400 KeV. It is advantageous to work at an ion dosage of $9 \times 10^{16}$ atoms/cm$^2$ and an ion energy of 150 KeV.

The titanium-silicon layer 2 incorporated as a foreign-element layer by implantation in the titanium surface does not form an additional layer on the said surface, and consequently there is no change in the shape or accuracy of fit of a workpiece made from the titanium-ceramic adhesive composite system.

Also there are no changes in the physical or chemical properties of the total workpiece through implantation of silicon ions 4. On the contrary, only the titanium-ceramic contact zone is subjected to the desired modifications. Chemically speaking, ion implantation is a "non-equilibrium process", i.e. introduction of the foreign element is not subject to any thermodynamic limitation resulting from solubility equilibrium or atomic diffusion rates. Consequently, conventionally insoluble elements can be mixed by this process and, with regard to the chosen silicon ion 4, the obtainable concentrations are much higher than those corresponding to its solubility (less than 1 atom/% in titanium).

A silicon concentration sufficient to passivate the titanium surface 1 can be obtained by ion implantation. Advantageously here too, the silicon ions 4 are incorporated in the form of silicon aggregates in the titanium-silicon layer 2.

The temperature of the solid titanium structure during ion implantation is controllable and can be kept below 100° C., thus eliminating thermal influences which might affect workpieces with high accuracy of fit, due to possible allotropic conversion of the titanium-element structure from $\alpha$ to $\beta$ crystals.

The titanium-silicon layer 2 formed by ion implantation has excellent adhesive strength. It is possible to "freeze" the resulting chemical compound, since it is largely unaffected by thermodynamic laws.

Crystalline, non-metallic materials were thermally applied to the thus-processed titanium surface 1 and an adhesive bond was made therewith.

The following crystalline non-metallic inorganic materials are suitable: glass-ceramic materials, non-oxidic ceramic materials or oxidic ceramic materials. These materials can be applied to the surface 1 of a titanium structure, i.e. of pure titanium or titanium alloy, processed by implantation of silicon ions 4, and have much higher adhesive strength than when applied to non-processed structures. This will bw explained in further detail hereinafter, using the titanium-ceramic adhesive composite system according to the invention as an example.

One suitable titanium alloy is a titanium-vanadium-aluminum alloy having the following composition:

Ti—6Al—4V

It is assumed that the titanium alloy used conforms to the special requirements of the application and the possible processing technique. The titanium-ceramic adhesive composite system forms the surface 1 of structure which already have the shape of the workpiece ready for use. This is possible since, as already described, no additional layers are applied to the titanium surface 1 and the temperature of the titanium base structure is kept below 100° C. during ion implantation, so that no deformation through heating can occur.

Tests have shown that the titanium-ceramic adhesive composite system is particularly suitable for use in a dental prosthesis.

In the process for producing a titanium-ceramic adhesive composite system for use in a dental prosthesis, silicon ions 4 are introduced between the titanium ions 5 in the surface 1 of a pure titanium structure by implantation with ion beams 3, as a result of which a titanium-silicon layer 2 is formed in the surface 1 of the structure in the penetration layer of ion implantation.

The use of pure titanium is necessary for medical dental reasons.

A dental ceramic material especially devised for lining titanium was fired on the thus-prepared titanium surface 1 in accordance with the manufacturer's instructions.

Four basic firing cycles are needed for producing the titanium-ceramic adhesive composite system for a dental prosthesis. The firing cycles are:

1st cycle: bonder and/or wash-firing material

2nd cycle: base-material firing

3rd cycle: Dentine firing

4th cycle: Gloss firing

Other firing cycles are optional, such as aesthetic colour firing.

The following is a discussion of some examples of experimental procedure and results in the production of the titanium ceramic adhesive composite system for dental prostheses.

EXAMPLE 1

Preparation of the Titanium

In the present tests, non-alloyed titanium Ti 2 was used as per Table 1.

TABLE 1

Chemical composition of pure titanium to DIN 17850

| Material | | Chemical composition (% by weight) | | | | |
|---|---|---|---|---|---|---|
| Symbol | Number | $O_{max}$ | $H_{max}$ | $C_{max}$ | $H_{max}$ | Ti |
| Ti 1 | 3.07025 | 0.12 | 0.05 | 0.06 | 0.013 | remainder |
| Ti 2 | 3.07035 | 0.18 | 0.05 | 0.06 | 0.013 | remainder |
| Ti 2 | 3.07055 | 0.25 | 0.05 | 0.06 | 0.013 | remainder |
| Ti 4 | 3.07065 | 0.35 | 0.05 | 0.06 | 0.013 | remainder |

The physical properties of non-alloyed titanium are given in Table 2.

TABLE 2

Physical properties of non-alloyed titanium

| | |
|---|---|
| Atomic number | 22 |
| Atomic weight | 47.8 |
| Density (g/ccm) | 4.51 |
| Melting-point (° C.) | 1688 |
| Boiling-point (° C.) | 3260 |
| Vickers hardness | 80–105 |
| Tensile strength (MPa) | |
| Cold-worked | 450 |
| Cast | 050 |
| Elongation at break (%) | 15–20 |
| Thermal expansion coefficient (1/K) | $9.6 \times 10^{-6}$ |
| Thermal conductivity (W/mK) | 21.4 |

In the SCHMITZ-SCHULMEYER shear test, non-alloyed, drawn titanium Ti 2 was used in the form of elongated cuboids with an edge length of 5.9×5.9×1000 mm.

Cubes measuring 5.9×5.9 mm were cut off these cuboids. The critical advantage in the present test is that a cavity-free workpiece is obtained with a surface free from α-case. This procedure avoids the difficulty of defined removal of this layer and possible resulting non-uniform dimensional stability of the testpieces.

The surfaces for lining with ceramic were subjected to two different mechanical surface treatments.

Firstly the surface was machined with a staggered cutter, making a defined thickness of material, in order to remove the surface titanium oxide layer. Next, half the testpieces were roughened by blasting with corundum, grain size 250 μm.

The grain size was at the upper limit of the range from 50 to 250 μm.

Further tests showed that after removal of the surface titanium oxide layer, roughening can be effected with ground monocrystalline silicon $Si_{mon}$ with a mesh size of 50 to 300 μm under a protective-gas atmosphere.

The roughening of the surface 1 and the accompanying increase in the titanium-ceramic adhesive surface and increase in mechanical adhesion was omitted in the case of the other half of the testpieces. The purpose of this control batch was to test whether the chemical adhesive strength of the ceramic lining was increased by ion modification.

After a quarter-hour "rest" for passivating the titanium surface, it was cleaned with a steam jet cleaner.

EXAMPLE 2

Surface Modification by Ion Implantation

The two batches, which had received different mechanical surface treatment, were divided and half were modified by ion implantation. The implantation equipment was a LINEAR ION IMPLANTER LION 6000, made by Messrs LEYBOLD AG of Hanau.

Ion implantation was effected with silicon ions 4, it being assumed that the penetration zone between the titanium atoms 5 and the silicon ions 4 occurred in the surface 1 of the testpieces. The resulting titanium-silicon layer 2, owing to its chemical properties, blocked reactions on the titanium surface 1 (FIG. 1).

The ion dosage was $3 \times 10^{17}$ atoms/cm$^2$ and the ion energy was 150 KeV.

The preferred range was between $1 \times 10^{12}$ and $1 \times 10^{18}$ atoms/cm$^2$ for the ion dosage and 30 to 400 KeV for the ion energy.

The testpieces not modified by silicon implantation served as a control batch for testing the effects of ion implantation on the titanium-ceramic adhesive bond.

EXAMPLE 3

The Titanium Ceramics Used

The following special titanium ceramics were used for lining the testpieces:

VITA TITANKERAMIK, produced by Messrs VITA ZAHNFABRIK/Bad Säckingen, and

TIBOND, produced by Messrs DE TREY/DENTSPLY/Dreieich.

Table 3 gives the composition of "VITA TITANKERAMIK" titanium ceramic material in % by mass:

TABLE 3

VITA TITANKERAMIK, composition in % by mass

|  | Bonder | Opacifier | Dentine/melt |
| --- | --- | --- | --- |
| SiO$^2$ | 61.2–64.0 | 59.9–62.1 | 67.1–69.0 |
| Al$_2$O$_3$ | 6.2–6.6 | 7.3–7.7 | 7.2–7.5 |
| K$_2$O | 3.2–3.7 | 7.1–7.6 | 8.2–8.7 |
| Na$_2$O | 5.1–5.4 | 5.3–5.7 | 6.0–6.3 |
| CaO | 4.5–5.0 | 1.0–1.3 | 1.1–1.4 |
| B$_2$O$_3$ |  | 6.1–6.9 | 8.0–8.4 |
| BaO | 2.0–2.3 | 0.1–0.3 |  |
| SnO$_2$ | 2.1–2.5 | 2.1–2.7 |  |
| MgO | 0.5–0.8 | 8.0–8.4 |  |
| TiO$_2$ |  | 8.0–8.4 |  |

The following Table 4 gives the firing parameters as stated by Messrs VITA ZAHNFABRIK, Bad Säckingen, in the processing instructions and as used during the firing cycles.

TABLE 4

VITA TITANKERAMIK, firing parameters

| VITA TITAN-KERAMIK | Standby temperature, °C. | Firing temperature, °C. | Pre-drying time | Heating-up time | Holding time | Vacuum | Slow cooling |
| --- | --- | --- | --- | --- | --- | --- | --- |
| Bonder | 600 | 800 | 6 min | 1 min | 7 min | 7 min | + |
| Base/opac. | 400 | 790 | 2 min | 3 min | 1 min | 4 min | + |
| Dentine | 400 | 770 | 6 min | 7 min | 1 min | 8 min | + |
| Adjustment | 400 | 770 | 6 min | 7 min | 1 min | 8 min | + |
| Gloss | 400 | 770 | 3 min | 3 min | 2 min | — | + |

TABLE 5

TIBOND, composition in % by mass

|  | Bonder | Opacifier | Dentine/melt |
| --- | --- | --- | --- |
| SiO$^2$ | 63–65 | 44.1–45.5 | 64–66 |
| Al$_2$O$_3$ | 6–7 | 8.4–9.1 | 12–13 |
| K$_2$O | 7–8 | 6.3–7.0 | 7–9 |
| Na$_2$O | 5–6 | 4.2–4.9 | 5–6 |
| Li$_2$O | 2–3 | 0.7–1.4 | 1–2 |
| CaO | 3–4 | 1.1–2.1 | 1–2 |
| B$_2$O$_3$ | 10–11 | 2.8–3.5 | 5–7 |

The next Table 6 gives the firing parameters as stated by Messrs DE TREY DENTSPLY/Dreieich in the instructions for use and as used during the firing cycles:

TABLE 6

TIBOND, firing parameters

| TIBOND | Standby temperature, °C. | Firing temperature, °C. | Pre-drying time | Heating-up time | Holding time | Vacuum |
| --- | --- | --- | --- | --- | --- | --- |
| Bonder | 650 | 780 | 2 min | 2 min | 3 min | 1 min |
| Base/opac. | 650 | 760 | 3 min | 3 min | 3 min | 2 min |
| Dentine | 650 | 750 | 6 min | 3 min | 2 min | 4 min |
| Adjustment | 650 | 750 | 6 min | 3 min | 2 min | 4 min |
| Gloss | 650 | 740 | 3 min | 3 min | 2 min | — |

EXAMPLE 4

Testing the Strength of the Bond

The adhesive strength of ceramic linings on titanium skeletons can be investigated in a mechanical fracture test for determining the bonding strength which, if the testpiece production is substantially exactly reproducible, give a minimum scatter in results with minimum technical outlay.

In addition, the arrangement of testpieces and the test rig should be sufficient to obtain an exact quantitative assessment of the bonding strength or adhesive strength. The shear test after SCHMITZ-SCHULMEYER meets these requirements and also, via the test arrangement and procedure, gives exact information about the actual adhesive strength between the metal and ceramic, in its technical aspects, eliminating interfering influences such as radial stresses and bending moments in the ceramic veneering and plastic or elastic deformation inside the metal skeletons.

A modified version of the shear test after SCHMITZ-SCHULMEYER was used in the experiments.

As already explained, the testpieces for the shear test were in the shape of cubes with an edge length of 5.9 mm. The titanium testpieces were veneered with ceramic material on one surface of the cube, half the surface being covered whereas the other half of the surface was not covered.

In contrast to the surface-ground load punch specified by SCHMITZ-SCHULMEYER, our load punch was in the form of a pressure hammer-edge ground at an angle of 45°. Owing to its shape, the point of application of the force of the load punch could be positioned without difficulty in reproducible manner very near (<1 mm) the transition from ceramic to metal. This procedure reduced the inevitable bending moment to a minimum and prevented the load punch from being accidentally positioned far enough from the bonder/base material interface for the measured results to be influenced by the adhesive strength between the bonder and the base material or the bonding strength thereof.

The cubes lined with ceramics were fixed in a special shear tool and tested in a mechanical pressure and bending testing machine, it being possible at any time to move the testpieces into the same position relative to the load punch. The load punch was positioned very near the metal edge and the ceramic material was loaded by the punch at a rate of advance of 1.0 mm/min until the base material completely sheared.

EXAMPLE 5

SEM Reflected Images and Semi-Quantitative EDAX Analyses

SEM reflected images and semi-quantitative EDAD analyses of pretreated testpieces were prepared at typical places on the bond.

Figure 6:
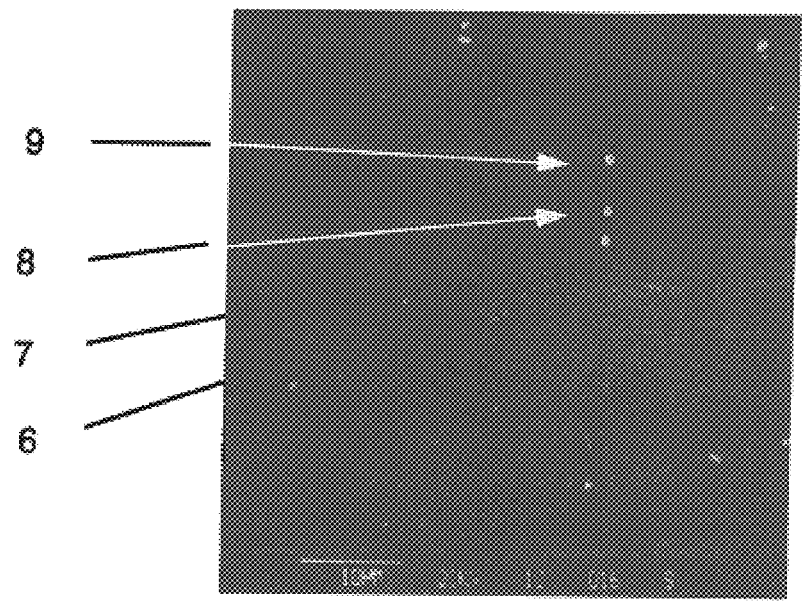
FIG. 6 shows the arrangement of the measuring points in the EDAX analyses.

FIG. 6 shows the arrangement of the measured points in the EDAX analysis. Point 6 is about 2 $\mu$m inside the titanium structure and point 7 is on the visible titanium-ceramic interface. Points 8, 9 are 2 $\mu$m and 5 $\mu$m in the ceramic and in the bonder material respectively. The region around the titanium-ceramic contact zone was additionally tested for presence of caverns with a high content of aluminum. The results of the spot EDAX tests on the SEM sectional views using the prepared reflected electron images were compared with the adhesive strength results of the shear test.

EXAMPLE 6

Production of Testpieces for the Shear Test After SCHMITZ-SCHULMEYER

The testpieces, in accordance with their pre-treatment or surface conditioning, were divided into different test series, which could be classified in the two main groups for comparison, i.e. ion-implanted and non-ion-implanted titanium (Table 7).

TABLE 7

| Titanium-ceramic combination | | | |
| --- | --- | --- | --- |
| Titanium, ion-implanted | | Titanium, not ion-implanted | |
| α-Al$_2$O$_3$-treated | Not α-Al$_2$O$_2$-treated | α-Al$_2$O$_3$-treated | Not α-Al$_2$O$_3$-treated |
| TIBOND, TR/TC | | | |
| VITA/TITANKERAMIK TR/TC | | | |

A VACUMAT 300 vacuum ceramic furnace made by Messrs VITA was available for producing the ceramic lining. The ceramic furnace is microprocessor-controlled, freely programmable and completely automatic, and enabled all the firing parameters mentioned in Tables 4 and 6 to be put into practice.

After the testpiece surface for lining has been steam-jet cleaned, the ceramic materials were applied and fired in accrodance with the manufacturer's instructions, in four firing cycles for each testpiece:

1st cycle: bonder and/or wash-firing material
2nd cycle: base-material firing
3rd cycle: dentine firing
4th cycle: gloss firing The testpieces for the shear test were stored under two different conditions:

Half the testpieces were tested under normal conditions to DIN 50014-23/50-2 after dry storage (TR) for 24 hours.

The other half of the testpieces, after being ceramically veneered, were artificially aged by 5000 cyclic changes of thermal load (thermocycling, TC) in a water bath. The temperature difference was 50° C. (+5° C. <->+55° C.), the holding time at each temperature stage was 60 seconds and the transition time was 5 seconds. Immediately after artificial ageing, the adhesive strength was tested.

12 testpieces were prepared for each series, and 10 testpieces were selected at random for evaluation when required.

EXAMPLE 7

Production of the testpieces for the SEM-EDAX analysis

Test plates measuring 5×10×3 mm were prepared for the SEM-EDAX analysis.

A plate was allotted to each test series, and was subjected to the appropriate surface conditioning, processing, ceramic lining and storage, i.e. dry storage and thermocycling.

The testpieces were then embedded in an AKEMI-TRANSPARENT polyester-based synthetic resin made by Messrs JEAN WIRTZ. They were then sufficiently cooled after hardening and saw through the centre along the 10 mm edge of the test plate.

In the next operation the testpieces were machined on grinding wheels 25 cm in diameter and with various grain sizes (400 $\mu$m, 600 $\mu$m, 1000 $\mu$m, 1200 $\mu$m) on a grinding machine (type TF 250 by Messrs JEAN WIRTZ). Final high-gloss polishing was effected with DIAPAST, a diamond polishing paste having a grain size of 6 and 3 $\mu$m and diamond lubricating agent DIALUB SW, made by Messrs JEAN WIRTZ.

The thus-prepared testpieces were made conductive for the SEM investigation by sputtering them in a type SCD 040 apparatus made by Messrs BALZERS UNION.

The scanning-electron microscope tests were made in a 150 MKZ electron microscope made by Messrs CAMBRIDGE-STERECAN.

EXAMPLE 8

The shear test

The shear test after SCHMITZ-SCHULMEYER was made on a type 1435 ZWICK universal testing machine. 1000 N pressure gauge was used. The testpieces were screwed in the clamping device of the shearing tool, always in the same position relative to the load punch. The load punch was brought up to the ceramic surface and the ceramic was loaded at a rate of advance of 1 mm/min until it completely sheared.

The forces for shearing the ceramic were measured in Newtons and recorded on millimeter paper in a band recorder. The shear stress was calculated from the measured applied force and the surface area veneered with ceramic. After the shear test, accordingly, the surface area was measured with a stereo-microscope incorporating an ocular micrometer. The shear stress, serving as a measure of the adhesive strength, is given by the force divided by the surface area according to the formula:

$$\text{Shear stress} = \frac{N}{\text{mm}_2} = \frac{\text{Force } F[N]}{\text{Area } [\text{mm}_2]}$$

The shear stress in MPa (megapascals) was determined by a computer, directly connected to the ZWICK universal testing machine.

EXAMPLE 9

Results of the shear test after SCHMITZ-SCHULMEYER

Test 9.1; α-Al$_2$O$_3$-treated titanium/TIBOND

Table 8 gives the absolute values of the individual measurements on testpieces with Ceramic material: TIBOND Titanium surface: treated with α-Al$_2$O$_3$, ion-implanted,

TABLE 8

| n | TR τ/MPa | TC τ/MPa |
|---|---|---|
| 1 | 12.9 | 9.1 |
| 2 | 15.6 | 16.4 |
| 3 | 13.0 | 14.6 |
| 4 | 10.5 | 8.2 |
| 5 | 11.8 | 20.2 |
| 6 | 10.2 | 15.3 |
| 7 | 17.1 | 17.0 |
| 8 | 16.3 | 9.7 |
| 9 | 20.8 | 6.8 |
| 10 | 9.2 | 8.4 |

Meaning of symbols:
n: testpiece number
TR: dry storage
TC: thermocycling
τ: shear stress in MPa
The same symbols are used in the following Tables.

Table 9 shows the absolute values of the individual measurements on testpieces for Ceramic material: TIBOND Titanium surface: α-Al$_2$O$_3$-treated, not ion-implanted

TABLE 9

| n | TR τ/MPa | TC τ/MPa |
|---|---|---|
| 1 | 17.1 | 22.6 |
| 2 | 20.2 | 22.6 |
| 3 | 14.0 | 15.5 |
| 4 | 18.3 | 14.4 |
| 5 | 23.4 | 23.9 |
| 6 | 22.4 | 18.2 |
| 7 | 23.2 | 18.9 |
| 8 | 17.7 | 17.2 |
| 9 | 15.2 | 10.7 |
| 10 | 12.0 | 14.2 |

Figure 2:
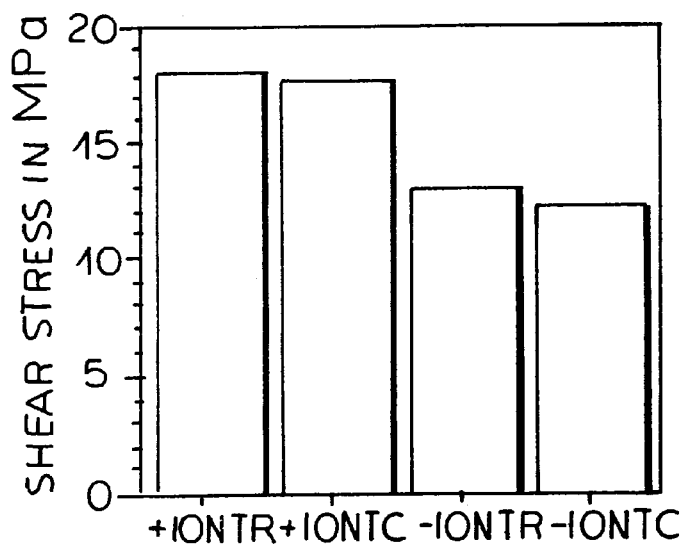
FIG. 2 is a graphic view of the median values in MPa of the strength of the bond in the combination between $\alpha$-Al$_3$O$_3$-treated titanium and TIBOND.

To this end, the graphic representation in FIG. 2 gives a general idea of the median values for the composite system between α-Al$_2$O$_3$-treated titanium and TIBOND titanium-ceramic material, together with a comparison between ion-implanted and non-ion-implanted surfaces in dependence on the storage conditions.

The median value for adhesive strength of the ion-implanted testpiece series was 18 MPa after dry storage and decreased to 17.7 MPa after thermocycling. By contrast the adhesive strength for non-ion-implanted control series decreased from 13 MPa to 12.2 MPa.

The percentage reduction in adhesive strength after ion implantation was 1.7%, considerably less than the 6.2% loss in adhesive strength without ion implantation.

A direct comparison between the ion-implanted and non-ion-implanted series under similar storage conditions showed an increase in adhesive strength after ion implantation of 27.8% after dry storage and 31.1% after thermocycling.

Test 9.2:

α-Al$_2$O$_3$-treated titanium/VITA TITANKERAMIK

Table 10 gives the absolute values of the individual measurements on testpieces for Ceramic material: VITA TITANKERAMIK Titanium surface: α-Al$_2$O$_3$-blasted, ion-implanted

TABLE 10

| n | TR τ/MPa | TC τ/MPa |
|---|---|---|
| 1 | 19.2 | 25.0 |
| 2 | 22.0 | 22.8 |
| 3 | 19.5 | 21.1 |
| 4 | 25.9 | 25.6 |
| 5 | 24.7 | 21.0 |
| 6 | 17.1 | 22.1 |
| 7 | 27.3 | 25.2 |
| 8 | 27.3 | 21.3 |
| 9 | 22.0 | 9.9 |
| 10 | 19.4 | 16.3 |

Table 11 gives the absolute values of individual measurements on the testpieces for Ceramic material: VITA TITANKERAMIK Titanium surface: α-Al$_2$-O$_3$-treated, non ion-implanted

TABLE 11

| n | TR τ/MPa | TC τ/MPa |
|---|---|---|
| 1 | 23.7 | 18.7 |
| 2 | 32.5 | 20.2 |
| 3 | 18.1 | 9.8 |
| 4 | 24.9 | 15.6 |
| 5 | 42.9 | 13.8 |
| 6 | 31.3 | 18.5 |
| 7 | 16.1 | 21.4 |
| 8 | 24.1 | 8.2 |
| 9 | 21.0 | 19.6 |
| 10 | 20.4 | 17.9 |

Figure 3:
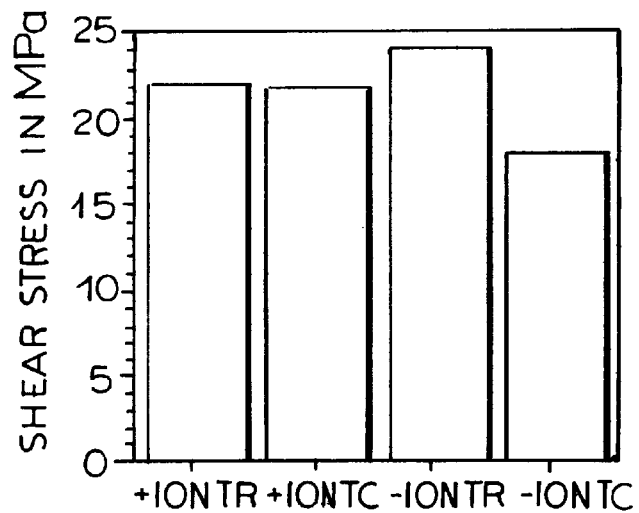
FIG. 3 is a graphic view of the median values in MPa of the strength of the bond in the combination between $\alpha$-Al$_3$O$_3$-treated titanium and VITA TITANKEKAMIK.

The graphic representation in FIG. 3 gives a general view of the median values of bonding strength in MPa, based on the measured values.

The value for ion-implanted titanium was 22 MPa after dry storage and 21.7 MPa after thermocycling.

The value for titanium not implanted with ions was 23.9 MPa after dry storage and 18.2 MPa after thermocycling.

A comparison between the percentage reductions in adhesive strength shows a value of 1.4% for the ion-implanted series as compared with 17.3% for a non-ion-implanted titanium surface. A comparison under similar storage conditions gives differing results.

Under dry storage, the adhesive strength of the ion-implanted series is 7.9% below the non-implanted series. After thermocycling the value for the non-implanted series is 16.1% lower than for ion-implanted titanium.

Test 9.3:

Titanium, not treated with α-Al$_2$O$_3$/TIBOND

Table 12 gives the absolute values for individual measurements on testpieces with Ceramic material; TIBOND Titanium surface: Not treated with α-Al$_2$O$_3$, ion-implanted

TABLE 12

| n | TR τ/MPa | TC τ/MPa |
|---|---|---|
| 1 | 9.0 | 14.4 |
| 2 | 14.7 | 9.8 |
| 3 | 7.8 | 15.6 |
| 4 | 12.0 | 15.0 |
| 5 | 10.2 | 7.8 |
| 6 | 15.0 | 12.8 |
| 7 | 14.9 | 9.8 |
| 8 | 11.5 | 13.5 |
| 9 | 12.6 | 11.6 |
| 10 | 13.8 | 12.0 |

Table 13 gives the absolute values of the individual measurements on testpieces for
Ceramic material: TIBOND
Titanium surface: Not treated with α-Al$_2$O$_3$, not ion-implanted

TABLE 13

| n | TR τ/MPa | TC τ/MPa |
|---|---|---|
| 1 | 14.4 | 7.5 |
| 2 | 10.2 | 12.0 |
| 3 | 9.7 | 14.3 |
| 4 | 6.6 | 9.6 |
| 5 | 12.1 | 6.9 |
| 6 | 10.8 | 7.1 |
| 7 | 8.2 | 8.8 |
| 8 | 9.9 | 10.7 |
| 9 | 9.1 | 7.7 |
| 10 | 8.7 | 8.3 |

Figure 4:
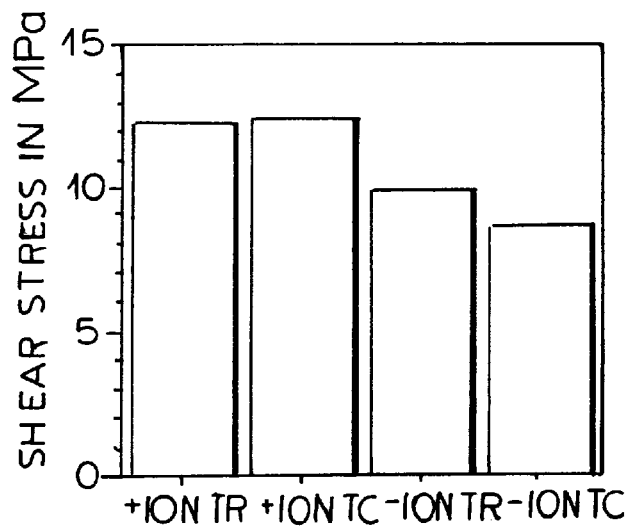
FIG. 4 is a graphic representation of the median values of the strength of the bond between titanium not treated with $\alpha$-Al$_2$O$_3$ and TIBOND.

The graphic representation in FIG. 4 gives a general view of the median values of bonding strength in MPa based on the measurements in Tables 12 and 13.

The titanium in these testpieces, modified by ion implantation, had an adhesive strength of 12.3 MPa after dry storage, increased to 12.4 MPa after thermocycling.

Without ion implantation, the values were 9.8 MPa for dry storage and 8.6 MPa after thermocycling.

A comparison between the change in adhesive strength with and without ion implantation and with modification shows a slight increase of 0.8%, as compared with a loss of 12.2% without modification.

Under dry storage, the value for non-ion-implanted titanium was 20.3% lower than for ion implantation. A percentage comparison after thermocycling gave a 30.7% lower value for non-ion-implanted titanium than for ion-modified titanium.

Test 9.4: Titanium, not treated with α-Al$_2$O$_3$/VITA TITANKERAMIK

Table 14 gives the absolute values of the individual measurements on testpieces with
Ceramic material: VITA TITANKERAMIK
Titanium surface: Not treated with α-Al$_2$O$_3$, ion-implanted

TABLE 14

| n | TR τ/MPa | TC τ/MPa |
|---|---|---|
| 1 | 14.3 | 12.4 |
| 2 | 17.9 | 10.2 |
| 3 | 24.5 | 17.9 |
| 4 | 12.8 | 27.6 |
| 5 | 16.3 | 22.8 |
| 6 | 8.8 | 22.4 |
| 7 | 22.1 | 16.1 |
| 8 | 15.7 | 19.4 |
| 9 | 13.0 | 22.7 |
| 10 | 13.6 | 25.9 |

Table 15 gives the absolute values of the individual measurements on testpieces for
Ceramic material: VITA TITANKERAMIK
Titanium surface: Not treated with α-Al$_2$O$_3$, not ion-implanted

TABLE 15

| n | TR τ/MPa | TC τ/MPa |
|---|---|---|
| 1 | 13.0 | 17.8 |
| 2 | 18.3 | 14.8 |
| 3 | 17.4 | 21.0 |
| 4 | 16.6 | 10.9 |
| 5 | 12.8 | 7.1 |
| 6 | 18.6 | 16.6 |
| 7 | 20.5 | 19.6 |
| 8 | 10.0 | 15.2 |
| 9 | 19.7 | 13.3 |
| 10 | 14.8 | 15.1 |

Figure 5:
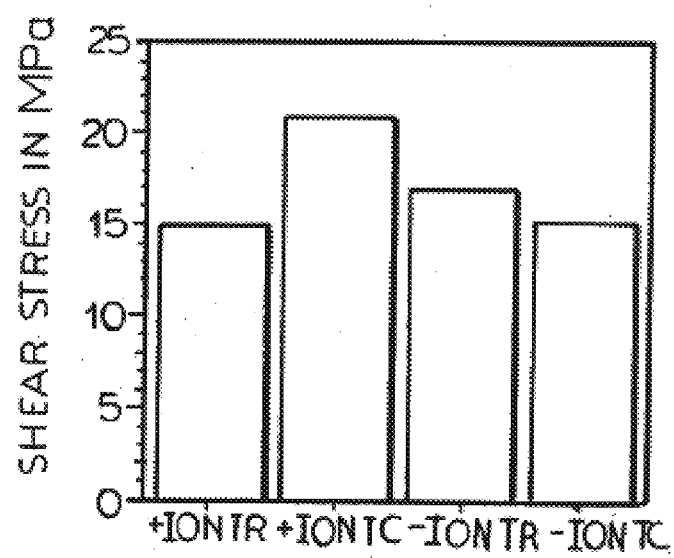
FIG. 5 is a graphic representation of the median values of the strength in MPa of the bond in the combination between titanium not treated with $\alpha$-Al$_2$O$_3$ and VITA TITANKERAMIK.

The graphic representation in FIG. 5 gives a general view of the median values of bond strength in MPa based on the measurements in Tables 14 and 15.

The adhesive strength of ion-implanted testpieces (20.9 MPa after thermocycling) was 39% above the value (15 MPa) after thermocycling. The adhesive strength of the non-modified control series was 17 MPa after dry storage and decreased by 10.6% to 15.2 MPa after thermocycling.

Under dry storage the value for ion-beam modified titanium was 11.8% below the value for non-modified titanium. After thermocycling the situation was reversed, and the values for the non-modified series were 27.3% below the values for the modified series.

EXAMPLE 10

Results of EDAX and SEM investigations

The arrangement of measured points in the EDAX analyses is shown in FIG. 6 and has already been described in Example 5, "SEM reflected image and semi-quantitative EDAX analyses", The SEM photographs as shown in FIGS. 7 to 14, depict the transition or contact zone between titanium and ceramic under 2000, 3200 and 3300 magnification. The titanium appears a an unstructured light-grey surface. By comparison the ceramic glass matrix has a darker, pale-blue colour. Metal oxides are recognisable from their colour, dark grey to anthracite. High density inclusions of heavy metal ions appear bright to white. The results are shown with reference to the thermocycled testpieces, and in the following Tables the figures were given for the most important elements (Ti, Si, Al). A direct comparison between testpieces modified by ion implantation with silicon and non-modified testpieces with the same mechanical surface treatment and the same ceramic lining material gives a vivid idea of the changes in the titanium-ceramic contact zone induced by the modification.

The proportion given as "remainder" in the following Tables denotes elements which could not be identified in the EDAX process.

Test 10.1: Titanium, treated with α-Al₂O₃/TIBOND, TC

Figure 7:
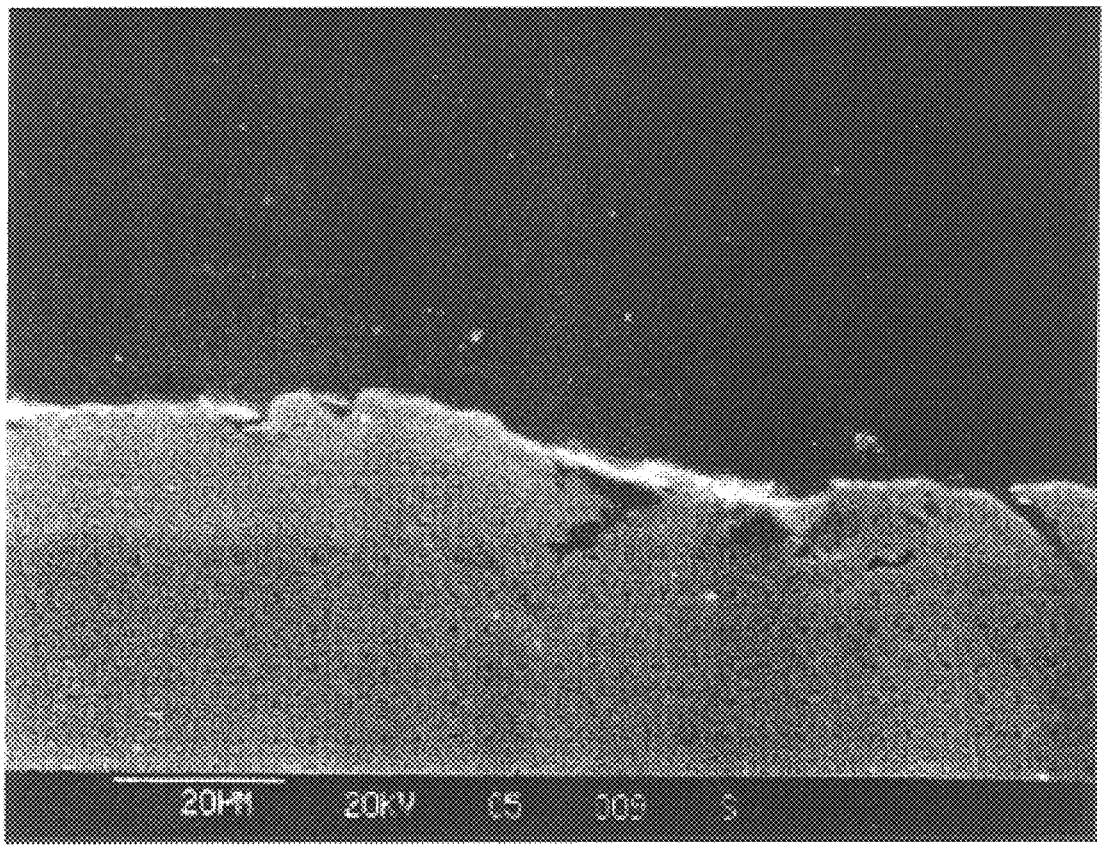
FIG. 7 is a SEM photograph of the combination between $\alpha$-Al$_2$O$_3$-treated titanium and TIBOND, TC, 512 magnification 3300:1 with ion implantation.

FIGS. 7 and 8 shown the SEM photographs of the combination: Titanium α-Al₂O₃-treated/TIBOND, with thermocycling TC.

FIGS. 7 and 8 show the titanium surface roughened by blasting with corundum, with good interlocking between the metal and the ceramic, indicating good wetting of the titanium surface by the bonder. The bonder for the ion-implanted testpiece has low porosity.

Without ion implantation (FIG. 8), a clearly visible, flaky crystalline intermediate layer appears above the titanium surface, with a width of about 6 μm, whereas practically no crystalline flakes can be made out after ion implantation (FIG. 7). The titanium and silicon concentrations at measured point 8 (FIG. 6) without ion implantation were correspondingly high. FIGS. 7 and 8 both show caverns in which the measured aluminium concentrations are high (32% for ion implantation and 92.2% without ion implantation).

The measured percentage concentrations of the stated elements are given in Table 16.

TABLE 16

Results of EDAX analysis for the combination: α-Al₂O₃-treated titanium/TIBOND, TC

| | 2 μm is the metal (measuring point 6) | | Contact zone (measuring point 7) | | 2 μm in the ceramic (measuring point 8) | | 5 μm in the ceramic (measuring-point 9) | |
|---|---|---|---|---|---|---|---|---|
| | +ION | −ION | +ION | −ION | +ION | −ION | +ION | −ION |
| Ti | 83.4 | 98.9 | 26.5 | 70.3 | 2.7 | 13.7 | 0.8 | 0.9 |
| Si | 6.4 | 0.0 | 20.3 | 2.3 | 40.0 | 51.1 | 34.4 | 38.1 |
| Al | 4.2 | 0.0 | 5.6 | 4.4 | 11.0 | 3.3 | 3.5 | 4.1 |
| Remainder | 3.3 | 1.1 | 24.8 | 15.3 | 23.3 | 31.1 | 40.1 | 48.6 |

Test 10.2: α-Al₂O₃-treated titanium/VITA TITANKERAMIK, TC

The SEM photograph is shown in FIGS. 9 and 10.

The titanium surface, roughened by blasting with corundum, shows good wetting between the bonder and titanium, as in the corresponding TIBOND series for comparison. A flaky-crystalline intermediate layer is clearly visible in the case of the testpieces not implanted with silicon (FIG. 10) whereas the contact zone conditioned by ion implantation does not show any comparable structures (FIG. 9). The EDEX analyses confirm the optical impression, the distribution of elements at measuring point 8 (FIG. 6) being particularly important. The titanium concentration at this place is considerably lower after ion implantation than without ion implantation. In this combination of titanium, ceramic and mechanical surface processing, there are still visible caverns with a high aluminium concentration of 66.4% without ion implantation and 71% with ion implantation.

Table 17 gives the measured values.

TABLE 17

Results of EDAX analysis for the combination: α-Al₂O₃-treated titanium/VITA TITANKERAMIK, TC

| | 2 μm is the metal (measuring point 6) | | Contact zone (measuring point 7) | | 2 μm in the ceramic (measuring point 8) | | 5 μm in the ceramic (measuring-point 9) | |
|---|---|---|---|---|---|---|---|---|
| | +ION | −ION | +ION | −ION | +ION | −ION | +ION | −ION |
| Ti | 100.00 | 100.00 | 49.7 | 61.8 | 1.5 | 9.6 | 0.9 | 1.4 |
| Si | 0.0 | 0.0 | 17.0 | 9.7 | 33.3 | 48.6 | 30.9 | 32.7 |
| Al | 0.0 | 0.0 | 4.4 | 8.6 | 3.2 | 5.4 | 7.8 | 4.6 |
| Remainder | 0.0 | 0.0 | 23.4 | 17.2 | 46.8 | 30.2 | 42.8 | 48.7 |

Test 10.3: Titanium not treated with α-Al₂O₃/TIBOND, TC

The SEM photographs are shown in FIGS. 11 and 12.

The metal surface is strikingly smooth, compared with the testpieces blasted with corundum. There is no influence on wetting with the bonder.

The titanium-ceramic contact zone not modified by the ion beam shows pronounced flaky-crystalline structures which extend relatively far into the bonder layer. At measuring point 8 without ion implantation, this EDAX analysis shows an extremely high concentration of titanium, whereas the silicon concentration is lower. By contrast with the testpieces treated with α-Al₂O₃, the concentration of non-identifiable residual elements on the edge of the titanium (measuring-point 7) is lower.

TABLE 18

Results of EDAX analysis for the combination: titanium not treated with α-Al₂O₃-TIBOND, TC

| | 2 μm is the metal (measuring point 6) | | Contact zone (measuring point 7) | | 2 μm in the ceramic (measuring point 8) | | 5 μm in the ceramic (measuring-point 9) | |
|---|---|---|---|---|---|---|---|---|
| | +ION | −ION | +ION | −ION | +ION | −ION | +ION | −ION |
| Ti | 98.8 | 100.0 | 88.8 | 81.2 | 1.2 | 41.5 | 0.6 | 1.7 |
| Si | 0.0 | 0.0 | 5.2 | 3.4 | 33.7 | 14.5 | 38.2 | 31.7 |
| Al | 0.0 | 0.0 | 1.2 | 0.7 | 4.5 | 2.2 | 3.2 | 5.9 |
| Remainder | 1.2 | 0.0 | 1.8 | 11.6 | 46.3 | 33.1 | 44.7 | 47.1 |

Test 10.4: Titanium, not treated with α-Al₂O₃/VITA TITANKERAMIK, TC

The SEM photographs are shown in FIGS. 13 and 14.

Marked differences are visible in this titanium-ceramic adhesive bond also. In accordance with the preceding observations, the bonder layer on titanium not conditioned by ion bombardment shows crystalline structures characterized by a grainy appearance. In this case also, these structures extend to the entire bonder layer and have high proportions of titanium (12%) at measuring point 8. By contrast in the case of ion-implanted titanium, the bonder layer is homogeneous and not structured. Correspondingly, only 1.2% of titanium was found 2 μm above the metal edge (measuring point 8).

In this case also, the concentration of residual elements measured at point 7 was lower than for the surfaces treated with α-Al₂O₃. As with all the other titanium-ceramic adhesive bonds, the integrity of the contact zone is good and the metal surface is completely wetted by the bonder.

TABLE 19

Results of EDAX analysis for the combination:
titanium not treated with α-Al$_2$O$_3$-VITA TITANKERAMIK, TC

| | 2 μm is the metal (measuring point 6) | | Contact zone (measuring point 7) | | 2 μm in the ceramic (measuring point 8) | | 5 μm in the ceramic (measuring point 9) | |
|---|---|---|---|---|---|---|---|---|
| | +ION | −ION | +ION | −ION | +ION | −ION | +ION | −ION |
| Ti | 98.1 | 100.0 | 79.1 | 96.5 | 1.2 | 12.1 | 1.0 | 1.3 |
| Si | 0.0 | 0.0 | 9.8 | 1.2 | 30.5 | 22.2 | 29.2 | 28.3 |
| Al | 0.0 | 0.0 | 1.2 | 0.0 | 2.8 | 2.3 | 2.7 | 5.1 |
| Remainder | 1.9 | 0.0 | 6.8 | 1.9 | 98.1 | 45.3 | 57.3 | 52.1 |

Conclusion

As the preceding test results show, the loss of adhesive strength, particularly under cyclic changes in temperature load, can be substantially avoided by the process of producing a titanium-ceramic adhesive composite system for dental prostheses and by the resulting titanium-ceramic adhesive bond for dental prostheses.

As previously shown, in the tests two different titanium-ceramic materials (TIBOND and VITA TITANKERAMIK) were fired on drawn, milled titanium Ti 2, the veneering surface being conditioned by implantation with silicon ions. In addition, titanium conventionally blasted with α-Al$_2$O$_3$ was compared with titanium which had not been treated with α-Al$_2$O$_3$. Test series having a veneering surface which had not been conditioned by an ion beam were used for comparison. After dry storage for 24 hours and after artificial aging by 5000 cyclic changes in temperature load, the adhesive strength of the ceramic veneering was tested in the SCHMITZ-SCHULMEYER shearing test.

Without ion implantation, the loss of adhesive strength as a result of thermocycling was statistically significant (6.2% to 17.3%). By contrast, in the case of an ion-implanted titanium surface after thermocycling, the change in values, with one exception, was not statistically significant (between a loss of 1.7% and an increase in 1.8% adhesive strength). The noteworthy increase in the case of VITA TITANKERAMIK was based on ion-implanted titanium not blasted with corundum. This series showed a highly significant increase in adhesive strength (39%).

Under dry storage there was no statistically significant improvement in the adhesive strength of ceramic on titanium due to ion implantation except in the case of TIBOND, whereas there was no change for VITA TITANKERAMIK and a slight impairment in the case of titanium treated with α-Al$_2$O$_3$.

After thermocycling, the values for all ion-modified test series were statistically significantly above those for non-modified test series.

A comparison between α-Al$_2$O$_3$-treated testpieces and non-treated testpieces after thermocycling shows that the non-treated testpieces after ion implantation had adhesive strengths comparable with that of α-Al$_2$O$_3$-treated testpieces without ion implantation.

The results of the EDAX analysis and scanning-electron microscope investigations of the titanium-ceramic contact zone confirm the good results of the shear test after SCHMITZ-SCHULMEYER. The diffusion of titanium and silicon in opposite directions and the resulting formation of flaky crystalline titanium silicides in the ceramic near the titanium surface, which was detectable in the case of test series not conditioned by ion implantation, was completely blocked by silicon implantation.

Since the titanium-silicon layer 2 in the surface 1 of the pure titanium structure is produced by ion implantation, the base member for a dental prosthesis can be shaped completely true to dimensions before implantation. It is then necessary only to apply the dental ceramic by firing.

The titanium silicon layer 2 can be applied to the entire structure. In the case of dental prostheses, the dental ceramic is applied by firing on individual sections only, particularly in the tooth region and in the region of contact with the mucous membrane. The applied titanium-silicon layer 2 also prevents titanium ions from escaping from the dental prosthesis base member.

The titanium-ceramic adhesive composite system is also advantageously applicable to structures or workpieces used at high-temperatures ranging from 600 to 3600° C.

In that case as before, silicon ions are introduced between the atoms 5 of titanium or the atoms 5 of titanium alloy in the surface of a pure titanium or titanium-alloy structure by implantation with ion beams 3. A titanium-silicon layer 2 is formed in the surface 1 of the structure in the ion implantation penetration zone. Crystalline, non-metallic inorganic materials are deposited on the titanium-silicon layer 2, and form an adhesive composite system. The silicon ions 4 can be incorporated in the form of silicon aggregates in the titanium-silicon layer 2.

Silicon ions 4 are implanted in the surface 1 of the pure titanium or titanium-alloy structure at an ion dosage of $1\times10^8$ to $1\times10^{18}$ atoms/cm$^2$, preferably $9\times10^{16}$ atoms/cm$^2$ and an ion energy of 30 to 400 KeV, preferably 150 KeV.

The crystalline, non-metallic inorganic materials consist of glass-ceramic materials, non-oxidic ceramic materials or oxidic-ceramic materials. By this means, the specific properties of titanium, i.e. its high strength and low weight, can be used also for workpieces intended for operation at high temperatures. One preferred application is to the production of workpieces for engines and propulsion units in motor-vehicle construction or in air and space travel.

On particular advantage in this application also is that the pure titanium or titanium-alloy structure before ion implantation is given the form of a workpiece for use at high temperatures from 600 to 3600° C. and, apart from thermal application of a crystalline, non-metallic inorganic material, no further processing of the structure is effected after the titanium-silicon layer 2 has formed in the surface 1 of the structure.

The titanium-ceramic adhesive composite system according to the invention also improves adhesive strength under changing thermal loads in the high-temperature range.

The use of the titanium-ceramic adhesive composite system is not restricted to the stated sector, but extends to all areas where a firm bond is required between applied non-metallic inorganic materials and a titanium base member even under thermal loads. This opens up an additional application to chemical apparatus, since in this case also some chemical processes operate at high temperatures.

More particularly, the applied material also prevents undesired chemical reactions with the material of the vessel in which the processes take place.

What is claimed is:

1. A process for producing a titanium-ceramic adhesive composite system characterized in that silicon ions are introduced into the surface (1) of a pure titanium or titanium-alloy structure by ion implantation with ion beams (3) between the atoms (5) of the titanium or the atoms (5) of the titanium alloy, by means of which a titanium-silicon layer (2) is formed in the surface (1) of the structure in the penetration layer of ion implantation, and crystalline non-metallic inorganic materials are thermally applied on to the titanium-silicon layer and an adhesive bond is made with the materials.

2. A process according to claim 1, characterized in that the silicon ions (4) are incorporated in the form of silicon aggregates in the titanium-silicon layer (2).

3. A process according to claim 1, characterized in that the crystalline non-metallic inorganic materials consist of glass-ceramic materials, non-oxidic ceramic materials or oxidic ceramic materials.

4. A process according to claim 1, characterized in that the titanium alloy used is a titanium-vanadium-aluminium alloy having the following composition: Ti-6A1-4V.

5. A process according to claim 1, characterized in that the titanium alloy is a titanium alloy conforming to the special requirements of the application and the possible production technique.

6. A process according to claim 1, characterized in that the implantation of silicon ions (4) into the surface (1) of the pure titanium or titanium-alloy structure is performed at an ion dosage of $1\times10^8$ to $1\times10^{18}$ atoms/cm$^2$ and an ion energy of 30 to 400 KeV.

7. A process according to claim 6, characterized in that the implantation of silicon ions (4) into the surface (1) of the pure titanium or titanium-alloy structure is performed at an ion dosage of $9\times10^{16}$ atoms/cm$^2$ and an ion energy of 150 KeV.

8. A process of producing a titanium-ceramic adhesive composite system according to claim 1, characterized in that for use in a dental prosthesis, silicon ions (4) are introduced into the surface (1) of a pure titanium structure by ion implantation with ion beams (3) between the atoms (5) of titanium, as a result of which a titanium-silicon layer (2) is formed in the surface (1) of the structure in the penetration layer of the ion implantation, and a dental ceramic for titanium veneering is fired on the titanium-silicon layer.

9. A process according to claim 8, characterized in that the implantation of silicon ions (4) into the surface (1) of the pure titanium structure is performed at an ion dosage of $1\times10^{12}$ to $1\times10^{18}$ atoms/cm$^2$ and an ion energy of 30 to 400 KeV.

10. A process according to claim 9, characterized in that the implantation of silicon ions (4) into the surface (1) of the pure titanium structure is carried out at an ion dosage of $3\times10^{17}$ atoms/cm$^2$ and an ion energy of 150 KeV.

11. A process according to claim 8, characterized in that the pure titanium contains the following proportions (in % by mass):

| | |
|---|---|
| $O_{max}$ | 0.12 |
| $N_{max}$ | 0.05 |
| $C_{max}$ | 0.06 |
| $H_{max}$ | 0.013 |
| Ti | Remainder |

12. A process according to claim 8, characterized in that before the ion implantation of the surface (1) of the pure titanium structure, the surface titanium oxide layer is removed by machining and is subsequently roughened in a protective gas atmosphere by ground monocrystalline silicon ($Si_{mon}$) having a mesh size of 50 to 300 µm.

13. A process according to claim 8, characterized in that after removal of the titanium oxide layer from the surface (1) of the pure titanium structure, the surface (1) is roughened by blasting with corundum ($\alpha$-Al$_2$O$_3$) having a particle size of 50–250 µm.

14. A process according to one or more of claim 8, characterized in that the pure titanium structure, before the ion implantation, is completely formed as a base member for a dental prosthesis and, apart from firing on the dental ceramic, no further treatment of the structure is carried out after the titanium-silicon layer (2) has formed in the surface (1) of the structure.

15. A process according to claim 8, characterized in that the titanium-silicon layer (2) is formed in the entire surface (1) of the pure titanium structure formed as the base member for a dental prosthesis, and the dental ceramic for the titanium veneering is fired on individual portions of the surface (1), the dental ceramic being fired on at least those portions of the base member for a dental prosthesis which form the tooth regions and the regions of contact with the mucous membrane.

16. A process according to claim 8, characterized in that the dental ceramic for the titanium veneering is fired on the titanium-silicon layer (2) in four firing cycles:

1st cycle: bonder and/or wash-firing material,

2nd cycle: base material firing;

3rd cycle: dentine firing;

4th cycle: gloss firing.

17. A titanium-ceramic adhesive composite system produced by the process according to claim 8, characterized in that for use as a dental prosthesis, the surface (1) of a pure titanium structure is formed as a titanium-silicon layer (2), wherein silicon ions (4) are introduced by ion implantation between the atoms (5) of the pure titanium and wherein a dental ceramic intended for titanium veneering is fired on the titanium-silicon layer (2).

18. A titanium-ceramic adhesive composite system according to claim 17, characterized in that the silicon ions (4) for forming the titanium-silicon layer (2) are introduced into the surface (1) of the pure titanium structure at an ion dosage of $1\times10^{12}$ to $1\times10^{18}$ atoms/cm$^2$ of silicon ions (4) and an ion energy of 30 to 400 KeV.

19. A titanium-ceramic adhesive composite system according to claim 18, characterized in that the silicon ions (4) for forming the titanium-silicon layer (2) are introduced into the surface (1) of the pure titanium structure at an ion dosage of $3\times10^{17}$ atoms/cm$^2$ and an ion energy of 150 KeV.

20. A titanium-ceramic adhesive composite system according to claim 17, characterized in that the pure titanium has the following composition (as % mass):

| | |
|---|---|
| $O_{max}$ | 0.12 |
| $N_{max}$ | 0.05 |
| $C_{max}$ | 0.06 |
| $H_{max}$ | 0.013 |
| Ti | Remainder |

21. A titanium-ceramic adhesive composite system according to one or more claim 17, characterized in that the pure titanium structure, before its surface (1) has been converted into a titanium-silicon layer (2), is made completely in the form of a base member for a dental prosthesis, and after the titanium-silicon layer (2) has formed, the dental ceramic is applied thereto by firing in a single treatment operation.

22. A titanium-ceramic adhesive composite system according to claim 17, characterized in that the titanium-silicon layer (2) is formed in the entire surface (1) of the pure titanium structure, which is in the form of the base member for a dental prosthesis, and the dental ceramic intended for the titanium veneering is fired on individual portions of the surface (1), the dental ceramic being fired at least on those portions of the base member for a dental prosthesis which form the tooth regions and the regions of contact with the mucous membrane.

23. A process for producing a titanium-ceramic adhesive composite system according to claim 1, characterized in that, for use in a high temperature range from 600 to 3600° C., silicon ions (4) are introduced into the surface (1) of a pure titanium or titanium-alloy structure by ion implantation with ion beams (3) between the atoms (5) of the titanium or the atoms (5) of the titanium alloy, as a result of which a titanium-silicon layer (2) is formed in the surface (1) of the structure in the penetration layer of the ion implantation, and crystalline non-metallic inorganic materials are thermally applied to the titanium-silicon layer and an adhesive bond is made with the materials.

24. A process according to claim 23, characterized in that the silicon ions (4) are incorporated in the form of silicon aggregates in the titanium-silicon layer (2).

25. A process according to claim 23, characterized in that the crystalline non-metallic inorganic materials consist of glass-ceramic materials, non-oxidic ceramic materials or oxidic ceramic materials.

26. A process according to claim 23, characterized in that the implantation of silicon ions (4) into the surface (1) of the pure titanium or titanium-alloy structure is performed at an ion dosage of $1\times10^8$ to $1\times10^{18}$ atoms/cm$^2$ an ion energy of 30 to 400 KeV.

27. A process according to claim 26, characterized in that the implantation of silicon ions (4) into the surface (1) of the pure titanium or titanium alloy structure is performed at an ion dosage of $9\times10^{16}$ atoms/cm$^2$ and an ion energy of 150 KeV.

28. A process according to claim 23, characterized in that before the ion implantation, the pure titanium or titanium-alloy structure is made in the form of a workpiece for use in a high-temperature range of 600 to 3600° C. and, apart from thermal application of a crystalline non-metallic inorganic material, no further treatment of the structure is carried out after the titanium-silicon layer (2) has been formed in the surface (1) of the structure.

29. A process according to claim 28, characterized in that the workpiece is used in engines and power units of motor vehicles and in air and space travel.

30. A titanium-ceramic adhesive composite system produced by the process according to claim 23, characterized in that, for use in a high-temperature range from 600 to 3600° C., the surface (1) of a pure titanium or titanium-alloy structure is formed as a titanium-silicon layer (2), the silicon ions (4) being introduced by ion implantation between the atoms (5) of the titanium or the atoms (5) of the titanium alloy and wherein a crystalline non-metallic inorganic material is thermally deposited on to the titanium-silicon layer (2).

31. A titanium-ceramic adhesive composite system according to claim 30, characterized in that the silicon ions (4) are incorporated in the form of silicon aggregates into the titanium-silicon layer (2).

32. A titanium-ceramic adhesive composite system according to claim 30, characterized in that the crystalline non-metallic inorganic materials consist of glass-ceramic materials, non-oxidic ceramic materials or oxidic ceramic materials.

33. A titanium-ceramic adhesive composite system according to claim 30, characterized in that the implantation of silicon ions (4) into the surface (1) of the pure titanium or titanium-alloy structure is carried out at an ion dosage of $1\times10^8$ to $1\times10^{18}$ atoms/cm$^2$ and an ion energy of 30 to 400 KeV.

34. A titanium-ceramic adhesive composite system according to claim 33, characterized in that the implantation of silicon ions (4) into the surface (1) of the pure titanium or titanium-alloy structure is carried out at an ion dosage of $9\times10^{16}$ atoms/cm$^2$ and an ion energy of 150 KeV.

35. A titanium-ceramic adhesive composite system according to claim 30, characterized in that before the ion implantation, the pure titanium or titanium-alloy structure is made in the form of a workpiece for use in a high-temperature range from 600 to 3600° C. and, apart from thermal application of a crystalline, non-metallic inorganic material, no further treatment of the structure is carried out after the titanium-silicon layer (2) has formed in the surface (1) of the structure.

36. A titanium-ceramic adhesive composite system according to claim 35, characterized in that the workpiece is usable in engines and power units in motor-vehicle construction and in air and space travel.

37. A titanium-ceramic adhesive composite system produced by the process according to claim 1, characterized in that the surface (1) of a pure titanium or titanium-alloy structure is made in the form of a titanium-silicon layer (2), the silicon ions (4) being introduced by ion implantation between the atoms (5) of the titanium or the atoms (5) of the titanium alloy and wherein a crystalline non-metallic inorganic material is thermally deposited on to the titanium-silicon layer (2).

38. A titanium-ceramic adhesive composite system according to claim 37, characterized in that the silicon ions (4) for producing the titanium-silicon layer (2) are introduced into the surface (1) of the pure titanium or titanium-alloy structure at an ion dosage of $1\times10^8$ to $1\times10^{18}$ atoms/cm$^2$ and an ion energy of 30 to 400 KeV.

39. A titanium-ceramic adhesive composite system according to claim 38, characterized in that the silicon ions (4) are introduced into the surface (1) of the pure titanium or titanium-alloy structure at an ion dosage of $9\times10^{16}$ atoms/cm$^2$ and an ion energy of 150 KeV.

* * * * *